US012692491B2

(12) United States Patent
Wong et al.

(10) Patent No.: US 12,692,491 B2
(45) Date of Patent: Jul. 28, 2026

(54) NUCLEIC ACID COMPLEXES FOR SCREENING BARCODED COMPOUNDS

(71) Applicant: Children's Medical Center Corporation, Boston, MA (US)

(72) Inventors: Wesley Philip Wong, Cambridge, MA (US); Clinton H. Hansen, Brighton, MA (US)

(73) Assignee: Children's Medical Center Corporation, Boston, MA (US)

( * ) Notice: Subject to any disclaimer, the term of this patent is extended or adjusted under 35 U.S.C. 154(b) by 981 days.

(21) Appl. No.: 17/845,914

(22) Filed: Jun. 21, 2022

(65) Prior Publication Data

US 2023/0045556 A1     Feb. 9, 2023

Related U.S. Application Data

(63) Continuation of application No. 15/578,962, filed as application No. PCT/US2016/035563 on Jun. 2, 2016, now Pat. No. 11,396,650.

(60) Provisional application No. 62/169,826, filed on Jun. 2, 2015.

(51) Int. Cl.
| | |
|---|---|
| *C12N 15/10* | (2006.01) |
| *C12N 15/11* | (2006.01) |
| *C12N 15/115* | (2010.01) |
| *C40B 20/04* | (2006.01) |
| *C40B 40/08* | (2006.01) |

(52) U.S. Cl.
CPC .......... *C12N 15/1065* (2013.01); *C12N 15/11* (2013.01); *C12N 15/111* (2013.01); *C12N 15/115* (2013.01); *C40B 40/08* (2013.01); *C12N 2310/16* (2013.01); *C12N 2310/34* (2013.01); *C12N 2310/3517* (2013.01); *C12N 2320/10* (2013.01); *C40B 20/04* (2013.01)

(58) Field of Classification Search
CPC ... C12N 15/1065; C12N 15/11; C12N 15/111; C12N 15/115; C12N 2310/16; C12N 2310/34; C12N 2310/3517; C12N 2320/10; C40B 40/08; C40B 20/04
See application file for complete search history.

(56) References Cited

U.S. PATENT DOCUMENTS

| | | |
|---|---|---|
| 5,571,677 A | 11/1996 | Gryaznov |
| 5,635,352 A | 6/1997 | Urdea et al. |
| 5,888,731 A | 3/1999 | Yager et al. |
| 5,902,724 A | 5/1999 | Lane et al. |

(Continued)

FOREIGN PATENT DOCUMENTS

| | | |
|---|---|---|
| JP | H06-508753 A | 10/1994 |
| JP | 2000-312589 A | 8/2000 |

(Continued)

OTHER PUBLICATIONS

Kenakin (Journal of Biomolecular Screening 15(2); 2010, p. 119-130).*

(Continued)

*Primary Examiner* — Robert H Havlin
(74) *Attorney, Agent, or Firm* — Wolf, Greenfield & Sacks, P.C.

(57) ABSTRACT

The invention provides compositions comprising nucleic acid complexes for use in screening compounds based on their ability to modulate binding interactions, wherein the compounds are barcoded.

19 Claims, 5 Drawing Sheets

Specification includes a Sequence Listing.

(56)        References Cited

U.S. PATENT DOCUMENTS

| 6,143,504 | A | 11/2000 | Das et al. |
| 6,232,066 | B1 | 5/2001 | Felder et al. |
| 6,251,660 | B1 | 6/2001 | Muir et al. |
| 6,569,306 | B1 | 5/2003 | Read et al. |
| 6,770,698 | B1 | 8/2004 | Chu et al. |
| 8,129,119 | B2 | 3/2012 | Jarrell et al. |
| 8,491,454 | B2 | 7/2013 | Wong et al. |
| 8,795,143 | B2 | 8/2014 | Wong et al. |
| 9,255,905 | B1 | 2/2016 | Mellors et al. |
| 9,914,958 | B2 | 3/2018 | Wong et al. |
| 9,994,839 | B2 | 6/2018 | Lo et al. |
| 10,919,037 | B2 | 2/2021 | Wong et al. |
| 11,198,900 | B2 | 12/2021 | Koussa et al. |
| 11,396,650 | B2 | 7/2022 | Wong et al. |
| 11,591,636 | B2 | 2/2023 | Wong et al. |
| 11,713,483 | B2 | 8/2023 | Wong et al. |
| 12,077,807 | B2 | 9/2024 | Chandrasekaran et al. |
| 12,123,869 | B2 | 10/2024 | Hansen et al. |
| 12,331,349 | B2 | 6/2025 | Wong et al. |
| 2002/0081744 | A1 | 6/2002 | Chan et al. |
| 2002/0182717 | A1 | 12/2002 | Karlsson et al. |
| 2003/0143549 | A1 | 7/2003 | Yang et al. |
| 2003/0186301 | A1 | 10/2003 | Christian et al. |
| 2006/0194240 | A1 | 8/2006 | Arnold, Jr. et al. |
| 2006/0257958 | A1 | 11/2006 | Bruno |
| 2007/0026423 | A1 | 2/2007 | Koehler et al. |
| 2007/0037152 | A1 | 2/2007 | Drmanac |
| 2007/0117109 | A1 | 5/2007 | Rothemund |
| 2007/0154899 | A1 | 7/2007 | Coull et al. |
| 2007/0184054 | A1 | 8/2007 | Greif et al. |
| 2007/0281367 | A1 | 12/2007 | Hennessy et al. |
| 2008/0038725 | A1 | 2/2008 | Luo et al. |
| 2008/0044834 | A1* | 2/2008 | Heyduk ............... G01N 33/542 |
| | | | 435/6.11 |
| 2008/0131870 | A1 | 6/2008 | Allawi et al. |
| 2008/0312103 | A1 | 12/2008 | Nemoto et al. |
| 2009/0087838 | A1 | 4/2009 | Reif et al. |
| 2009/0118140 | A1 | 5/2009 | Suzara |
| 2009/0286694 | A1 | 11/2009 | Zainiev et al. |
| 2010/0015608 | A1 | 1/2010 | Kolpashchikov |
| 2010/0035247 | A1 | 2/2010 | Burton |
| 2010/0206730 | A1 | 8/2010 | Hunkapiller et al. |
| 2010/0216658 | A1 | 8/2010 | Chaput et al. |
| 2011/0086774 | A1 | 4/2011 | Dunaway |
| 2011/0268654 | A1 | 11/2011 | Hilderbrand et al. |
| 2013/0004523 | A1 | 1/2013 | Zubarev et al. |
| 2013/0130884 | A1 | 5/2013 | Wong et al. |
| 2013/0196341 | A1 | 8/2013 | Neely et al. |
| 2013/0310260 | A1 | 11/2013 | Kim et al. |
| 2013/0344508 | A1 | 12/2013 | Schwartz et al. |
| 2014/0255939 | A1* | 9/2014 | Wong .................. C12Q 1/6804 |
| | | | 536/23.1 |
| 2014/0284213 | A1 | 9/2014 | Sabin et al. |
| 2014/0302532 | A1 | 10/2014 | Wilson et al. |
| 2015/0027894 | A1 | 1/2015 | Puleo et al. |
| 2015/0093836 | A1 | 4/2015 | Suzuki et al. |
| 2015/0099650 | A1 | 4/2015 | Sood et al. |
| 2015/0292007 | A1 | 10/2015 | Church et al. |
| 2015/0361422 | A1 | 12/2015 | Sampson et al. |
| 2017/0369935 | A1 | 12/2017 | Koussa et al. |
| 2018/0135043 | A1 | 5/2018 | Wong et al. |
| 2018/0223344 | A1 | 8/2018 | Chandrasekaran et al. |
| 2018/0274001 | A1 | 9/2018 | Efcavitch et al. |
| 2018/0291434 | A1 | 10/2018 | Wong et al. |
| 2019/0048409 | A1 | 2/2019 | Wong et al. |
| 2019/0070604 | A1 | 3/2019 | Wong et al. |
| 2020/0116712 | A1 | 4/2020 | Hansen et al. |
| 2020/0340033 | A1 | 10/2020 | Wong et al. |
| 2021/0355483 | A1 | 11/2021 | Chee et al. |
| 2023/0146476 | A1 | 5/2023 | MacDonald et al. |
| 2024/0018577 | A1 | 1/2024 | Wong et al. |
| 2024/0076715 | A1 | 3/2024 | Wong et al. |
| 2025/0003957 | A1 | 1/2025 | Hansen et al. |
| 2025/0034619 | A1 | 1/2025 | Chandrasekaran et al. |

FOREIGN PATENT DOCUMENTS

| JP | 2003-219897 | A | 8/2003 |
| JP | 2005-536234 | A | 12/2005 |
| JP | 2008-259453 | A | 10/2008 |
| JP | 2009-521230 | | 6/2009 |
| WO | WO 1993/01313 | A1 | 1/1993 |
| WO | WO 1998/18961 | A1 | 5/1998 |
| WO | WO 00/40751 | A2 | 7/2000 |
| WO | WO 2004/016767 | A2 | 2/2004 |
| WO | WO 2007/076128 | A2 | 7/2007 |
| WO | WO 2009/045906 | A2 | 4/2009 |
| WO | WO 2011/005221 | A1 | 1/2011 |
| WO | WO 2011/153211 | A1 | 12/2011 |
| WO | WO 2012/057689 | A1 | 5/2012 |
| WO | WO 2012/058638 | A2 | 5/2012 |
| WO | WO 2013/010023 | A2 | 1/2013 |
| WO | WO 2013/067489 | A1 | 5/2013 |
| WO | WO 2014/011800 | A1 | 1/2014 |
| WO | WO 2014/160192 | A1 | 10/2014 |
| WO | WO 2015/006626 | A1 | 1/2015 |
| WO | WO 2015/040009 | A1 | 3/2015 |
| WO | WO 2015/164602 | A2 | 10/2015 |
| WO | WO 2016/089588 | A1 | 6/2016 |
| WO | WO 2016/164866 | A1 | 10/2016 |
| WO | WO 2016/196824 | A1 | 12/2016 |
| WO | WO 2017/003950 | A2 | 1/2017 |
| WO | WO 2017/139409 | A1 | 8/2017 |
| WO | WO 2017/147398 | A1 | 8/2017 |
| WO | WO 2017/165647 | A1 | 9/2017 |
| WO | WO 2018/106721 | A1 | 6/2018 |
| WO | WO 2019/100080 | A1 | 5/2019 |

OTHER PUBLICATIONS

International Search Report and Written Opinion for PCT/US2016/035563 mailed Sep. 21, 2016.

International Preliminary Report on Patentability for PCT/US2016/035563 mailed Dec. 14, 2017.

[No Author Listed], Wikipedia Entry, "Xhol." May 14, 2014. Retrieved from the internet. <https://en.wikipedia.org/w/index/php?title=Xhol&oldid=608536958>. Retrieved on Oct. 18, 2016.

Aaij et al., The gel electrophoresis of DNA. Biochim Biophys Acta. May 10, 1972;269(2):192-200.

Bellot et al., Recovery of intact DNA nanostructures after agarose gel-based separation. Nat Methods. Mar. 2011;8(3):192-4. doi: 10.1038/nmeth0311-192.

Bishop et al., Electrophoretic separation of viral nucleic acids on polyacrylamide gels. J Mol Biol. Jun. 28, 1967;26(3):373-87.

Bustamante et al., Entropic elasticity of lambda-phage DNA. Science. Sep. 9, 1994;265(5178):1599-600.

Bustamante et al., Ten years of tension: single-molecule DNA mechanics. Nature. Jan. 23, 2003;421(6921):423-7.

Butko et al., Detection of Ligand-Induced Conformational Changes in Oligonucleotides by Second-Harmonic Generation at a Supported Lipid Bilayer Interface. Anal Chem. Nov. 1, 2016;88(21):10482-10489. Epub Oct. 12, 2016. Accepted Manuscript, 23 pages.

Chandrasekaran et al., Label-free Detection of Specific Nucleic Acid Sequences using DNA Nanoswitches. The RNA Institute , University at Albany, State University of New York.

Chandrasekaran et al., Programmable DNA Nanoswitches for Detection of Nucleic Acid Sequences. ACS Sens., 2016, 1 (2), pp. 120-123.

Cheng et al., Early pregnancy factor in cervical mucus of pregnant women. Am J Reprod Immunol. Feb. 2004;51(2):102-5.

Chilkoti et al., Molecular Origins of the Slow Streptavidin-Biotin Dissociation Kinetics. J Am Chem Soc. 1995;117(43):10622-8.

Chivers et al., A streptavidin variant with slower biotin dissociation and increased mechanostability. Nat Methods. May 2010;7(5):391-3. doi: 10.1038/nmeth.1450. Epub Apr. 11, 2010.

Cho et al., A genomic-scale view of the cAMP response element-enhancer decoy: a tumor target-based genetic tool. Proc Natl Acad Sci U S A. Nov. 26, 2002;99(24):15626-31. Epub Nov. 18, 2002.

Conde et al., Implantable hydrogel embedded dark-gold nanoswitch as a theranostic probe to sense and overcome cancer multidrug

(56)　　　　　References Cited

OTHER PUBLICATIONS resistance. Proc Natl Acad Sci U S A. Mar. 17, 2015;112(11):E1278-87. doi: 10.1073/pnas.1421229112. Epub Mar. 2, 2015.

Deniz et al., Single-molecule biophysics: at the interface of biology, physics and chemistry. J R Soc Interface. Jan. 6, 2008;5(18):15-45.

Devaraj et al., Biomedical applications of tetrazine cycloadditions. Acc Chem Res. Sep. 20, 2011;44(9):816-27. doi: 10.1021/ar200037t. Epub May 31, 2011.

Doshi et al., In vitro nanobody discovery for integral membrane protein targets. Sci Rep. Oct. 24, 2014;4:6760. doi: 10.1038/srep06760.

Douglas et al., A logic-gated nanorobot for targeted transport of molecular payloads. Science. Feb. 17, 2012;335(6070):831-4. doi: 10.1126/science.1214081.

Douglas et al., Self-assembly of DNA into nanoscale three-dimensional shapes. Nature. May 21, 2009;459(7245):414-8. doi: 10.1038/nature08016.

Evans et al., Dynamic strength of molecular adhesion bonds. Biophys J. Apr. 1997;72(4):1541-55.

Evans et al., Forces and bond dynamics in cell adhesion. Science. May 25, 2007;316(5828):1148-53.

Evans, Probing the relation between force—lifetime—and chemistry in single molecular bonds. Annu Rev Biophys Biomol Struct. 2001;30:105-28.

Fang et al., Tuning surface states to achieve the modulated fluorescence of carbon dots for probing the activity of alkaline phosphatase and immunoassay of alpha-fetoprotein. Sensors and Actuators B: Chemical. 2018;257:620-628.

França et al., A review of DNA sequencing techniques. Q Rev Biophys. May 2002;35(2):169-200.

Green, Avidin and streptavidin. Methods Enzymol. 1990;184:51-67.

Greenleaf et al., High-resolution, single-molecule measurements of biomolecular motion. Annu Rev Biophys Biomol Struct. 2007;36:171-90.

Halvorsen et al., Binary DNA nanostructures for data encryption. PLoS One. 2012;7(9):e44212. doi: 10.1371/journal.pone.0044212. Epub Sep. 11, 2012.

Halvorsen et al., Cross-platform comparison of nucleic acid hybridization: toward quantitative reference standards. Anal Biochem. Nov. 15, 2014;465:127-33. doi: 10.1016/j.ab.2014.08.001. Epub Aug. 12, 2014.

Halvorsen et al., Massively Parallel Single-Molecule Manipulation Using Centrifugal Force. Biophys J. Jun. 2, 2010;98(11):L53-5.

Halvorsen et al., Nanoengineering a single-molecule mechanical switch using DNA self-assembly. Nanotechnology. Dec. 9, 2011;22(49):494005. doi: 10.1088/0957-4484/22/49/494005. Epub Nov. 21, 2011.

Halvorsen, Probing Weak Single-Molecule Interactions: Development and Demonstration of a New Instrument. Boston University, College of Engineering dissertation. 2007: 102 pages.

Hanke et al., Entropy loss in long-distance DNA looping. Biophys J. Jul. 2003;85(1):167-73.

Hansen et al., Nanoswitch-linked immunosorbent assay (NLISA) for fast, sensitive, and specific protein detection. PNAS. Sep. 26, 2017;114(39):10367-10372. Supporting Information, 4 pages.

Hassur et al., UV shadowing—a new and convenient method for the location of ultraviolet-absorbing species in polyacrylamide gels. Anal Biochem. May 1974;59(1):162-4.

Hellman et al., Electrophoretic mobility shift assay (EMSA) for detecting protein-nucleic acid interactions. Nat Protoc. 2007;2(8):1849-61.

Hopwood et al., Integrated microfluidic system for rapid forensic DNA analysis: sample collection to DNA profile. Anal Chem. Aug. 15, 2010;82(16):6991-9. doi: 10.1021/ac101355r.

Idili et al., Programmable pH-triggered DNA nanoswitches. J Am Chem Soc. Apr. 23, 2014;136(16):5836-9. doi: 10.1021/ja500619w. Epub Apr. 9, 2014. Abstract only.

Jones et al., Nanomaterials. Programmable materials and the nature of the DNA bond. Science. Feb. 20, 2015;347(6224):1260901. doi: 10.1126/science.1260901.

Jung et al., Binding and Dissociation Kinetics of Wild-Type and Mutant Streptavidins on Mixed Biotin-Containing Alkylthiolate Monolayers. Langmuir. Nov. 28, 2000;16(24): 9421-32.

Khalil et al., Single M13 bacteriophage tethering and stretching. Proc Natl Acad Sci U S A. Mar. 20, 2007;104(12):4892-7. Epub Mar. 13, 2007.

Kim et al., A mechanically stabilized receptor-ligand flex-bond important in the vasculature. Nature. Aug. 19, 2010;466(7309):992-5. doi: 10.1038/nature09295.

Kleiner et al., Small-molecule discovery from DNA-encoded chemical libraries. Chem Soc Rev. Dec. 2011;40(12):5707-17. doi: 10.1039/c1cs15076f. Epub Jun. 14, 2011.

Klumb et al., Energetic roles of hydrogen bonds at the ureido oxygen binding pocket in the streptavidin-biotin complex. Biochemistry. May 26, 1998;37(21):7657-63.

Koch et al., Prospects and limitations of the rosette inhibition test to detect activity of early pregnancy factor in the pig. J Reprod Fertil. May 1985;74(1):29-38.

Koussa et al., DNA nanoswitches: a quantitative platform for gel-based biomolecular interaction analysis. Nat Methods. Feb. 2015;12(2):123-6. doi: 10.1038/nmeth.3209. Epub Dec. 8, 2014.

Koussa et al., Protocol for sortase-mediated construction of DNA-protein hybrids and functional nanostructures. Methods. May 15, 20145;67(2):134-41. doi: 10.1016/j.ymeth.2014.02.020. Epub Feb. 22, 2014.

Kufer et al., Single-molecule cut-and-paste surface assembly. Science. Feb. 1, 2008;319(5863):594-6. doi:10.1126/science.1151424.

Leier et al., Cryptography with DNA binary strands. Biosystems. Jun. 2000;57(1):13-22.

Lubken et al., Multiplexed Continuous Biosensing by Single-Molecule Encoded Nanoswitches. Nano Lett. Apr. 8, 2020;20(4):2296-2302. doi: 10.1021/acs.nanolett.9b04561. Epub Mar. 12, 2020.

Mcdonell et al., Analysis of restriction fragments of T7 DNA and determination of molecular weights by electrophoresis in neutral and alkaline gels. J Mol Biol. Feb. 15, 1977;110(1):119-46.

Modi et al., A DNA nanomachine that maps spatial and temporal pH changes inside living cells. Nat Nanotechnol. May 2009;4(5):325-30. doi: 10.1038/nnano.2009.83. Epub Apr. 6, 2009. Abstract only.

Morton et al., Early pregnancy factor. Semin Reprod Endocrinol. May 1992;10:72-82.

Morton et al., Rosette inhibition test: A multicentre investigation of early pregnancy factor in humans. J Reprod Immunol. Sep. 1982;4(5):251-61.

Neuman et al., Single-molecule force spectroscopy: optical tweezers, magnetic tweezers and atomic force microscopy. Nat Methods. Jun. 2008;5(6):491-505. doi: 10.1038/nmeth.1218.

Papadakis et al., Acoustic characterization of nanoswitch structures: application to the DNA Holliday Junction. Nano Lett. Dec. 8, 2010;10(12):5093-7. doi: 10.1021/nl103491v. Epub Nov. 1, 2010.

Park et al., Dual blockade of cyclic AMP response element-(CRE) and AP-1-directed transcription by CRE-transcription factor decoy oligonucleotide. gene-specific inhibition of tumor growth. J Biol Chem. Jan. 15, 1999;274(3):1573-80.

Pei et al., A DNA nanostructure-based biomolecular probe carrier platform for electrochemical biosensing. Adv Mater. Nov. 9, 2010;22(42):4754-8. doi: 10.1002/adma.201002767.

Ping, High Performing assay using antibody-conjugated DNA nanoswitches detects proteins. MRS Bulletin. 2017;42:780. 1 page.

Porchetta et al., Programmable Nucleic Acid Nanoswitches for the Rapid, Single-Step Detection of Antibodies in Bodily Fluids. J Am Chem Soc. Jan. 24, 2018;140(3):947-953. doi: 10.1021/jacs.7b09347. Epub Jan. 9, 2018.

Quek et al., Mechanically controlled binary conductance switching of a single-molecule junction. Nat Nanotechnol. Apr. 2009;4(4):230-4. doi: 10.1038/nnano.2009.10. Epub Mar. 1, 2009.

Ritort, Single-molecule experiments in biological physics: methods and applications. J Phys Condens Matter. Aug. 16, 2006;18(32):R531-83. doi:10.1088/0953-8984/18/32/R01. Epub Jul. 25, 2006.

Rothemund, Folding DNA to create nanoscale shapes and patterns. Nature. Mar. 16, 2006;440(7082):297-302.

Sacca et al., DNA origami: the art of folding DNA. Angew Chem Int Ed Engl. Jan. 2, 2012;51(1):58-66. doi: 10.1002/anie.201105846. Epub Dec. 7, 2011.

(56) References Cited

OTHER PUBLICATIONS

Seeman, DNA in a material world. Nature. Jan. 23, 2003;421(6921):427-31.

Seeman, Nanomaterials based on DNA. Annu Rev Biochem. 2010;79:65-87. doi: 10.1146/annurev-biochem-060308-102244.

Shroff et al., Biocompatible force sensor with optical readout and dimensions of 6 nm3. Nano Lett. Jul. 2005;5(7):1509-14.

Shroff et al., Optical measurement of mechanical forces inside short DNA loops. Biophys J. Mar. 15, 2008;94(6):2179-86. Epub Dec. 7, 2007.

Smith et al., Overstretching B-DNA: the elastic response of individual double-stranded and single-stranded DNA molecules. Science. Feb. 9, 1996;271(5250):795-9.

Strunz et al., Dynamic force spectroscopy of single DNA molecules. Proc Natl Acad Sci U S A. Sep. 28, 1999;96(20):11277-82.

Su et al., Nucleic acid fluorescent probes for biological sensing. Appl Spectrosc. Nov. 2012;66(11):1249-62. doi: 10.1366/12-06803. Review.

Svoboda et al., Direct observation of kinesin stepping by optical trapping interferometry. Nature. Oct. 21, 1993;365(6448):721-7.

Thorne, Electrophoretic separation of polyoma virus DNA from host cell DNA. Virology. Jun. 1966;29(2):234-9.

Thuring et al., A freeze-squeeze method for recovering long DNA from agarose gels. Anal Biochem. May 26, 1975;66(1):213-20.

Wiita et al., Force-dependent chemical kinetics of disulfide bond reduction observed with single-molecule techniques. Proc Natl Acad Sci U S A. May 9, 2006;103(19):7222-7. Epub Apr. 27, 2006.

Winfree et al., Design and self-assembly of two-dimensional DNA crystals. Nature. Aug. 6, 1998;394(6693):539-44.

Wong et al., The effect of integration time on fluctuation measurements: calibrating an optical trap in the presence of motion blur. Opt Express. Dec. 11, 2006;14(25):12517-31.

Yang et al., An integratable microfluidic cartridge for forensic swab samples lysis. Forensic Sci Int Genet. Jan. 2014;8(1):147-58. doi: 10.1016/j.fsigen.2013.08.012. Epub Sep. 8, 2013.

Yang et al., Multiplexed single-molecule force spectroscopy using a centrifuge. Nat Commun. Mar. 17, 2016;7:11026(1-7). doi: 10.1038/ncomms11026. PubMed PMID: 26984516; PubMed Central PMCID: PMC4800429.

Zadeh et al., NUPACK: Analysis and design of nucleic acid systems. J Comput Chem. Jan. 15, 2011;32(1):170-3. doi: 10.1002/jcc.21596.

Zhang et al., Mechanoenzymatic cleavage of the ultralarge vascular protein, von Willebrand Factor. Science. Jun. 5, 2009;324(5932):1330-4.

Zheng et al., From molecular to macroscopic via the rational design of a self-assembled 3D Dna crystal. Nature. Sep. 3, 2009;461(7260):74-7. doi: 10.1038/nature08274.

Horn et al., Forks and combs and DNA: the synthesis of branched oligodeoxyribonucleotides. Nucleic Acids Res. Sep. 12, 1989;17(17):6959-67.

Meagher et al., Free-solution electrophoresis of DNA modified with drag-tags at both ends. Electrophoresis. May 2006;27(9):1702-12. doi: 10.1002/elps.200500554.

Mendoza et al., Probing protein structure by amino acid-specific covalent labeling and mass spectrometry. Mass Spectrom Rev. Sep.-Oct. 2009;28(5):785-815.

Pinheiro et al., Challenges and opportunities for structural DNA nanotechnology. Nat Nanotechnol. Nov. 6, 2011;6(12):763-72.

Silver et al., Tethered-bead, immune sandwich assay. Biosens Bioelectron. Jan. 15, 2015;63:117-123. Epub Jul. 11, 2014.

* cited by examiner

SEQUENCE LISTING

```
<160> NUMBER OF SEQ ID NOS: 3

<210> SEQ ID NO 1
<211> LENGTH: 12
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (1)..(1)
<223> OTHER INFORMATION: Xaa is Propargyl glycine

<400> SEQUENCE: 1

Xaa Leu Pro Glu Thr Gly His His His His His His
1               5                   10

<210> SEQ ID NO 2
<211> LENGTH: 4
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (4)..(4)
<223> OTHER INFORMATION: Xaa is Propargyl glycine

<400> SEQUENCE: 2

Gly Gly Gly Xaa
1

<210> SEQ ID NO 3
<211> LENGTH: 7
<212> TYPE: PRT
```

-continued

```
<213> ORGANISM: Artificial Sequence
<220> FEATURE:
<223> OTHER INFORMATION: Synthetic Polypeptide

<400> SEQUENCE: 3

Leu Pro Glu Thr Gly Gly Gly
1               5
```

NUCLEIC ACID COMPLEXES FOR SCREENING BARCODED COMPOUNDS

RELATED APPLICATIONS

This application is a continuation of U.S. application Ser. No. 15/578,962, filed Dec. 1, 2017, which is a national stage filing under 35 U.S.C. § 371 of International application number PCT/US2016/035563, filed Jun. 2, 2016, which claims the benefit under 35 U.S.C. § 119(e) of U.S. provisional application Ser. No. 62/169,826, filed Jun. 2, 2015, each of which is incorporated by reference herein in its entirety.

REFERENCE TO A SEQUENCE LISTING SUBMITTED AS A TEXT FILE VIA EFS-WEB

The instant application contains a Sequence Listing which has been submitted in ASCII format via EFS-Web and is hereby incorporated by reference in its entirety. Said ASCII copy, created on Jun. 21, 2022, is named C123370084US02-SEQ-MAT and is 1,136 bytes in size.

SUMMARY

Provided herein are methods for screening pluralities of compounds, including for example compound libraries, for compounds having particular binding activities. The screening methods provided herein may be used to identify compounds that bind to a target specifically (including to a target but not its related family members), compounds that bind to a target and induce an allosteric change in the target wherein the allosteric change enhances or interferes with the binding of the target to a ligand of the target, compounds that bind to a target and induce an allosteric change in the target that renders the target inactive (and thus able to bind to a ligand specific for the inactive form of the target), and the like.

One aspect of this disclosure provides a method comprising (1) allowing a target to contact and bind to a candidate target-specific ligand comprising a nucleic acid barcode, wherein the target and the candidate target-specific ligand are linked to a nucleic acid complex, (2) isolating a target bound to a candidate target-specific ligand, and (3) identifying the candidate target-specific ligand, wherein the nucleic acid complex comprises a single-stranded scaffold nucleic acid hybridized to a plurality of single-stranded oligonucleotides, wherein a first single-stranded oligonucleotide is linked to the target and a second single-stranded oligonucleotide is linked to the candidate target-specific ligand.

The candidate target-specific ligand is a compound that is being screened for its ability to bind to the target, and depending on the embodiment induce a change such as an allosteric change in the target. The ability of the target to bind to the target in a specific manner (for example, even in the presence of a decoy such as a moiety that is structurally related but not identical to the target) is typically not known prior to the performing the screening method.

In some embodiments, the method further comprises a plurality of candidate target-specific ligands, each comprising a unique barcode, and a plurality of nucleic acid complexes, and wherein the method is a method of screening candidate target-specific ligands for the ability to bind to the target.

Another aspect of the disclosure provides a method comprising (1) providing a nucleic acid complex conjugated to a target and a candidate target-specific ligand comprising a nucleic acid barcode, (2) incubating the nucleic acid complex in solution for a sufficient time to allow the target to bind to the candidate target-specific ligand, (3) isolating the nucleic acid complex having the target bound to the candidate target-specific ligand, and (4) identifying the candidate target-specific ligand, wherein the nucleic acid complex comprises a single-stranded scaffold nucleic acid hybridized to a plurality of single-stranded oligonucleotides, wherein a first single-stranded oligonucleotide is linked to the target and a second single-stranded oligonucleotide is linked to the candidate target-specific ligand.

In some embodiments of these and other aspects provided herein, the candidate target-specific ligand comprises an aptamer. In some embodiments, the aptamer is or comprises the nucleic acid barcode. In some embodiments, the candidate target-specific ligand is a non-aptamer. In some embodiments, the candidate target-specific ligand does not comprise nucleic acid except for the nucleic acid barcode to which it is attached. In some embodiments, the target-binding region of the candidate target-specific ligand is not composed of a nucleic acid.

In some embodiments of these and other aspects provided herein, the candidate target-specific ligand is a nucleic acid, such as an aptamer, and it comprises an amine modification, optionally at its 3' end. In some embodiments, the method further comprises crosslinking the candidate target-specific ligand to the bound target prior to isolating. Such crosslinking may occur through for example the amine modification at the 3' end of a nucleic acid based or nucleic acid containing candidate target specific ligand.

In some embodiments of these and other aspects provided herein, the candidate target-specific ligand comprises a DNA-encoded macrocycle. The candidate target-specific ligand may also be a nucleic acid encoded macrocycle. In some embodiments, the candidate target-specific ligand, such as a DNA-encoded macrocycle, is linked to the nucleic acid complex through a bridge oligonucleotide. In some embodiments, the bridge oligonucleotide comprises a first region that hybridizes to the scaffold of the nucleic acid complex and a second region that hybridizes to the DNA-encoded macrocycle. In some embodiments, the second region comprises deoxyinosine bases capable of binding to A, C, T and G nucleotide bases. In some embodiments, the bridge oligonucleotide comprises an amino-modification at its 3' end.

In some embodiments of these and other aspects provided herein, the candidate target-specific ligand comprises an mRNA-displayed nanobody. In some embodiments, the mRNA-displayed nanobody comprises a linker comprising a 3' terminal puromycin and a deoxythymine nucleotide modified with a methyl-tetrazine. In some embodiments, the scaffold of the nucleic acid complex comprises a trans-cyclooctene modification. In some embodiments, the mRNA-displayed nanobody is attached to the nucleic acid complex through a reaction between the methyl-tetrazine on the linker and the trans-cyclooctene modification on the scaffold.

In some embodiments, the nucleic acid complex is further conjugated to a decoy. In some embodiments, the target and the decoy are structurally similar but not identical to each other. In these embodiments, the method may be a competition screening assay since the target and the decoy compete for binding to the candidate target specific ligand. In some embodiments, the target and the decoy are members of a protein family.

In some embodiments of these and other aspects provided herein, the method is a drug screening method comprising a plurality of nucleic acid complexes each comprising an identical target and a different candidate target-specific ligand itself having a unique barcode.

Another aspect of this disclosure provides a method comprising (i) contacting (1) a nucleic acid complex conjugated to a first binding partner and a second binding partner with (2) a candidate allosteric ligand conjugated to a nucleic acid barcode, (ii) isolating a nucleic acid complex having the first binding partner bound to the second binding partner and to the candidate allosteric ligand, and (iii) identifying the candidate allosteric ligand, wherein the nucleic acid complex comprises a single-stranded scaffold nucleic acid hybridized to a plurality of single-stranded oligonucleotides, wherein a first single-stranded oligonucleotide in the plurality is linked to the first binding partner and a second single-stranded oligonucleotide in the plurality is linked to the second binding partner.

In some embodiments, the first binding partner and the second binding partner do not bind to each other unless the candidate allosteric ligand is bound to the first binding partner. In some embodiments, contacting occurs in solution. In some embodiments, the nucleic acid complex is isolated using gel electrophoresis.

In some embodiments, the candidate allosteric ligand is identified by the nucleic acid barcode. In some embodiments, the candidate allosteric ligand is identified using nucleic acid sequencing and/or nucleic acid amplification.

In some embodiments, the first binding partner and the second binding partner are covalently linked to the first and second single-stranded oligonucleotides respectively.

In some embodiments, the candidate allosteric ligand is in solution. In some embodiments, the candidate allosteric ligand is linked to a third single-stranded oligonucleotide in the nucleic acid complex.

In some embodiments, the method further comprises covalently attaching the candidate allosteric ligand to the first binding partner after the contacting step. In some embodiments, the method further comprises forming a loop between the regions of the nucleic acid complex located at or near the allosteric ligand and the first binding partner after the contacting step. In some embodiments, the method further comprises crosslinking the candidate allosteric ligand to the first binding partner after the contacting step.

Another aspect of this disclosure provides a method comprising (i) contacting (I) a plurality of nucleic acid complexes each conjugated to a first binding partner and a second binding partner with (2) a plurality of candidate allosteric ligands each conjugated to a distinct/unique nucleic acid barcode, (ii) physically separating (1) nucleic acid complexes having the first binding partner bound to the second binding partner and to the candidate allosteric ligand from (2) other nucleic acid complexes, and (iii) identifying the candidate allosteric ligand bound to the first binding partner, wherein each nucleic acid complex comprises a single-stranded scaffold nucleic acid hybridized to a plurality of single-stranded oligonucleotides, wherein a first single-stranded oligonucleotide in the plurality is linked to the first binding partner and a second single-stranded oligonucleotide in the plurality is linked to the second binding partner.

In some embodiments, the first binding partner and the second binding partner do not bind to each other unless the candidate allosteric ligand is bound to the first binding partner.

In some embodiments, contacting occurs in solution. In some embodiments, the nucleic acid complexes are physically separated using gel electrophoresis.

In some embodiments, the candidate allosteric ligand bound to the first binding partner is identified by its distinct/unique nucleic acid barcode. In some embodiments, the candidate allosteric ligand is identified using nucleic acid sequencing and/or nucleic acid amplification.

In some embodiments, the first binding partner and the second binding partner are covalently linked to the first and second single-stranded oligonucleotides respectively.

In some embodiments, the candidate allosteric ligand is in solution. In some embodiments, the nucleic acid complexes are identical to each other. In some embodiments, the candidate allosteric ligand is linked to the nucleic acid complex. In some embodiments, the nucleic acid complexes are not identical to each other.

In some embodiments, the plurality of candidate allosteric ligands is a library of candidate allosteric ligands.

In some embodiments, the method further comprises covalently attaching the candidate allosteric ligand to the first binding partner after the contacting step. In some embodiments, the method further comprises crosslinking the candidate allosteric ligand to the first binding partner after the contacting step.

Another aspect of this disclosure provides a method comprising (1) allowing a candidate target-specific ligand to contact and bind to a target or a decoy, wherein the candidate target-specific ligand is conjugated to a nucleic acid barcode, and wherein the candidate target-specific ligand, the target and the decoy are linked to a nucleic acid complex, (2) isolating a candidate target-specific ligand bound to a target using gel electrophoresis, (3) identifying the candidate target-specific ligand, wherein the nucleic acid complex comprises a single-stranded scaffold nucleic acid hybridized to a plurality of single-stranded oligonucleotides, wherein a first single-stranded oligonucleotide is linked to the target, a second single-stranded oligonucleotide is linked to the decoy, and a third single-stranded oligonucleotide is linked to the candidate target-specific ligand.

Another aspect of this disclosure provides a method comprising (1) providing a nucleic acid complex conjugated to a target, a decoy, and a candidate target-specific ligand conjugated to a nucleic acid barcode. (2) allowing the candidate target-specific ligand to bind to the target or the decoy, (3) isolating a nucleic acid complex comprising the target bound to the candidate target-specific ligand, and (4) identifying the candidate target-specific ligand, wherein the nucleic acid complex comprises a single-stranded scaffold nucleic acid hybridized to a plurality of single-stranded oligonucleotides, wherein a first single-stranded oligonucleotide is linked to the target, a second single-stranded oligonucleotide is linked to the decoy, and a third single-stranded oligonucleotide is linked to the candidate target-specific ligand.

In some embodiments, contacting occurs in solution. In some embodiments, the nucleic acid complex is isolated using gel electrophoresis.

In some embodiments, the candidate target-specific ligand is identified by the nucleic acid barcode. In some embodiments, the candidate target-specific ligand is identified using nucleic acid sequencing and/or nucleic acid amplification.

In some embodiments, the target and the decoy are structurally related to each other. In some embodiments, the target and the decoy are members of a protein family.

In some embodiments, the target, the decoy and/or the candidate target-specific ligand is/are covalently linked to the first, second and third single-stranded oligonucleotides respectively.

In some embodiments, the method further comprises covalently attaching the candidate target-specific ligand to the target after the contacting step. In some embodiments, the method further comprises crosslinking the candidate target-specific ligand to the target after the contacting step.

Another aspect of this disclosure provides a method comprising (i) incubating a plurality of nucleic acid complexes each conjugated to a target, a decoy and a candidate target-specific ligand conjugated to a distinct/unique nucleic acid barcode, (ii) physically separating (1) nucleic acid complexes having the target bound to the candidate target-specific ligand from (2) other nucleic acid complexes, and (iii) identifying the candidate target-specific ligand bound to the target, wherein each nucleic acid complex comprises a single-stranded scaffold nucleic acid hybridized to a plurality of single-stranded oligonucleotides, wherein a first single-stranded oligonucleotide in the plurality is linked to the target, a second single-stranded oligonucleotide in the plurality is linked to the decoy, and a third single-stranded oligonucleotide in the plurality is linked to the candidate target-specific ligand. In some embodiments, contacting occurs in solution.

In some embodiments, the nucleic acid complexes are physically separated using gel electrophoresis.

In some embodiments, the candidate target-specific ligand bound to the target is identified by its distinct/unique nucleic acid barcode. In some embodiments, the candidate target-specific ligand is identified using nucleic acid sequencing and/or nucleic acid amplification.

In some embodiments, the target and the decoy are covalently conjugated to the nucleic acid complex. In some embodiments, the candidate target-specific ligand is covalently conjugated to the nucleic acid complex. In some embodiments, each nucleic acid complex differs from other nucleic acid complexes in the plurality by the candidate target-specific ligand conjugated to the distinct/unique nucleic acid barcode. In some embodiments, candidate target-specific ligand is conjugated to the nucleic acid complex through the distinct/unique nucleic acid barcode.

In some embodiments, the method further comprises covalently attaching the candidate target-specific ligand to the target after the contacting step. In some embodiments, the method further comprises crosslinking the candidate target-specific ligand to the target after the contacting step.

Another aspect of this disclosure provides a method comprising (1) contacting a target with a candidate allosteric ligand conjugated to a nucleic acid barcode, wherein the target and optionally the candidate allosteric ligand are bound to a nucleic acid complex that is further bound to an active-target-specific binding partner and optionally an inactive-target-specific binding partner. (2) isolating a target bound to a candidate allosteric ligand and an active-target-specific binding partner, and (3) identifying the candidate allosteric ligand bound to the target, wherein the nucleic acid complex comprises a single-stranded scaffold nucleic acid hybridized to a plurality of single-stranded oligonucleotides, wherein a first single-stranded oligonucleotide is linked to the target and a second single-stranded oligonucleotide is linked to the active-target-specific binding partner.

In some embodiments, the candidate allosteric ligand is linked to a third single-stranded oligonucleotide in the nucleic acid complex. In some embodiments, the candidate allosteric ligand is in solution. In some embodiments, the candidate allosteric ligand is covalently linked to the bound target prior to isolating. In some embodiments, the target is covalently linked to the bound active-target-specific binding partner prior to isolating. In some embodiments, a target bound to a candidate allosteric ligand and an active-target-specific binding partner is isolated using gel electrophoresis.

Another aspect of this disclosure provides a method comprising combining a scaffold nucleic acid with a plurality of single-stranded oligonucleotides, each single-stranded oligonucleotide having a nucleotide sequence complementary to a sequence of the scaffold nucleic acid, under conditions that allow the single-stranded oligonucleotides to hybridize to the scaffold nucleic acid in a sequence-specific manner without overlap, to form a nucleic acid complex, wherein a first single-stranded oligonucleotide in the plurality is conjugated to a target and a second single-stranded oligonucleotide in the plurality is conjugated to a candidate ligand comprising a nucleic acid barcode.

In some embodiments, the candidate ligand is an aptamer. In some embodiments, the aptamer is the nucleic acid barcode. In some embodiments, the aptamer comprises the nucleic acid barcode. In some embodiments, the aptamer is attached to a nucleic acid barcode post-synthesis.

In some embodiments, the aptamer comprises an amine modification, optionally at its 3' end.

In some embodiments, the candidate ligand comprises a nucleic acid-encoded macrocycle such as a DNA-encoded macrocycle. In some embodiments, the second single-stranded oligonucleotide comprises a first region that hybridizes to the scaffold nucleic acid and a second region that hybridizes to the DNA-encoded macrocycle. In some embodiments, the second region comprises deoxyinosine bases capable of binding to A, C, T and G nucleotide bases. In some embodiments, the second single-stranded oligonucleotide comprises an amino-modification at its 3' end.

In some embodiments, the candidate ligand comprises an mRNA-displayed nanobody. In some embodiments, the mRNA-displayed nanobody comprises a linker comprising a 3' terminal puromycin and a deoxythymine nucleotide modified with a methyl-tetrazine. In some embodiments, the scaffold nucleic acid comprises a trans-cyclooctene modification.

In some embodiments, a third single-stranded oligonucleotide in the plurality is conjugated to a decoy. In some embodiments, the target and the decoy are structurally similar but not identical to each other. In some embodiments, the target and the decoy are members of a protein family.

In some embodiments of the various aspects provided herein, the single-stranded oligonucleotides in the plurality are present in an equimolar concentration that is about 10-fold greater than the molar concentration of the scaffold nucleic acid.

Another aspect of this disclosure provides a composition comprising a nucleic acid complex comprising a single-stranded scaffold nucleic acid hybridized to a plurality of single-stranded oligonucleotides, wherein a first single-stranded oligonucleotide is linked to a nucleic acid barcoded (e.g., DNA barcoded) library member, a second single-stranded oligonucleotide is linked to a target, and optionally a third single-stranded oligonucleotide is linked to a decoy or a binding partner that binds to an inactive form of the target, or a binding partner that binds to an active form of the target, or a binding partner that binds to an allosteric form of the target but not a native form of the target, or a binding partner that binds to a native form of the target but not an allosteric form of the target. The nucleic acid barcoded library member may be a barcoded aptamer, a DNA barcoded macrocycle, a barcoded mRNA display nanobody, or a barcoded small molecule, although it is not so limited.

Another aspect of this disclosure provides a composition comprising a plurality of nucleic acid complexes each having bound thereto a nucleic acid barcoded (e.g., DNA barcoded) library member, wherein the nucleic acid complex comprises a single-stranded scaffold nucleic acid hybridized to a plurality of single-stranded oligonucleotides, wherein a first single-stranded oligonucleotide is linked to the DNA barcoded library member.

In some embodiments, the DNA barcoded library member is a barcoded aptamer, a DNA barcoded macrocycle, a barcoded mRNA display nanobody, or a barcoded small molecule.

In some embodiments, the nucleic acid complexes comprise an identical target and optionally an identical decoy as that term is described herein.

In some embodiments, the nucleic acids complexes comprise an identical first binding partner and second binding partner.

These and other aspects and embodiments of the invention will be described in greater detail herein.

(middle) V2: Testing a library of potential allosteric modulators simultaneously, by labeling each allosteric ligand with a unique nucleic-acid-based bar code. Provided the allosteric ligand binds to the receptor with sufficiently high-affinity to enable extraction, compounds that dramatically increase or decrease the affinity of the receptor to its orthosteric ligand can be extracted and read out from the solution-based nanoswitch assay developed in Aim 1. (bottom) V3: Testing a library of potential allosteric ligands simultaneously, in which each ligand is labeled with a nucleic-acid-based bar code that also serves as a molecular tether to an individual DNA nanoswitch construct. This approach is particularly useful for finding allosteric ligands that have low affinity for the target receptor since the DNA tether will keep the local concentration near the receptor high, and will also enable the allosteric molecule to be extracted and identified even when it is not bound to the receptor.

Figure 8:
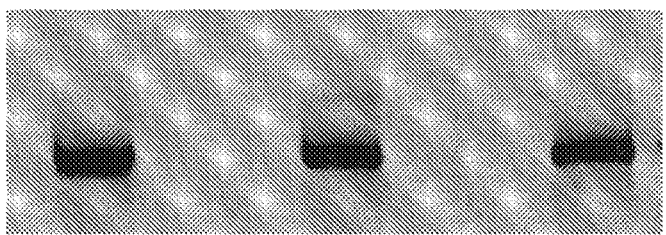

FIG. 8: Detection of allosteric modulation of β2-adrenoreceptor (β2AR) using nanoswitches. Here, the nanoswitch is constructed with β2AR attached to one position and a nanobody known to bind to the active form of β2AR [ref. 4] attached at another position. Looping is not detected without the presence of any drug (left). Looping is detected when the high-affinity allosterically-activating drug BI167107 is added (middle). When the high-affinity allosterically-inactivating drug ICI118.551 is added, looping is still not detected (right). Glutaraldehyde is used to fix loops before gel electrophoresis.

Figure 9:
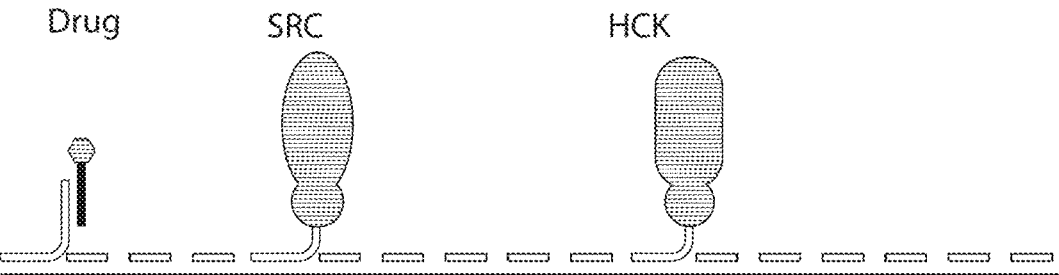

FIG. 9: Depiction of an highly specific compound screening assay based on DNA nanoswitch constructs. Testing a library of potential highly-specific ligands simultaneously, in which each ligand is labeled with a nucleic-acid-based bar code that also serves as a molecular tether to an individual DNA nanoswitch construct. Constructs are selected in which the drug binds to the protein of interest, while not interesting with the negative control protein. Here, Src is the protein of interest, while Hck is a highly homologous kinase in the same family. In order for increased selectivity, multiple copies of the negative control protein can be attached to the scaffold.

The color versions of the Figures are available in the file wrapper of the priority application U.S. 62/169,826, the entire contents of which are incorporated by reference herein.

DETAILED DESCRIPTION

Figure 1:
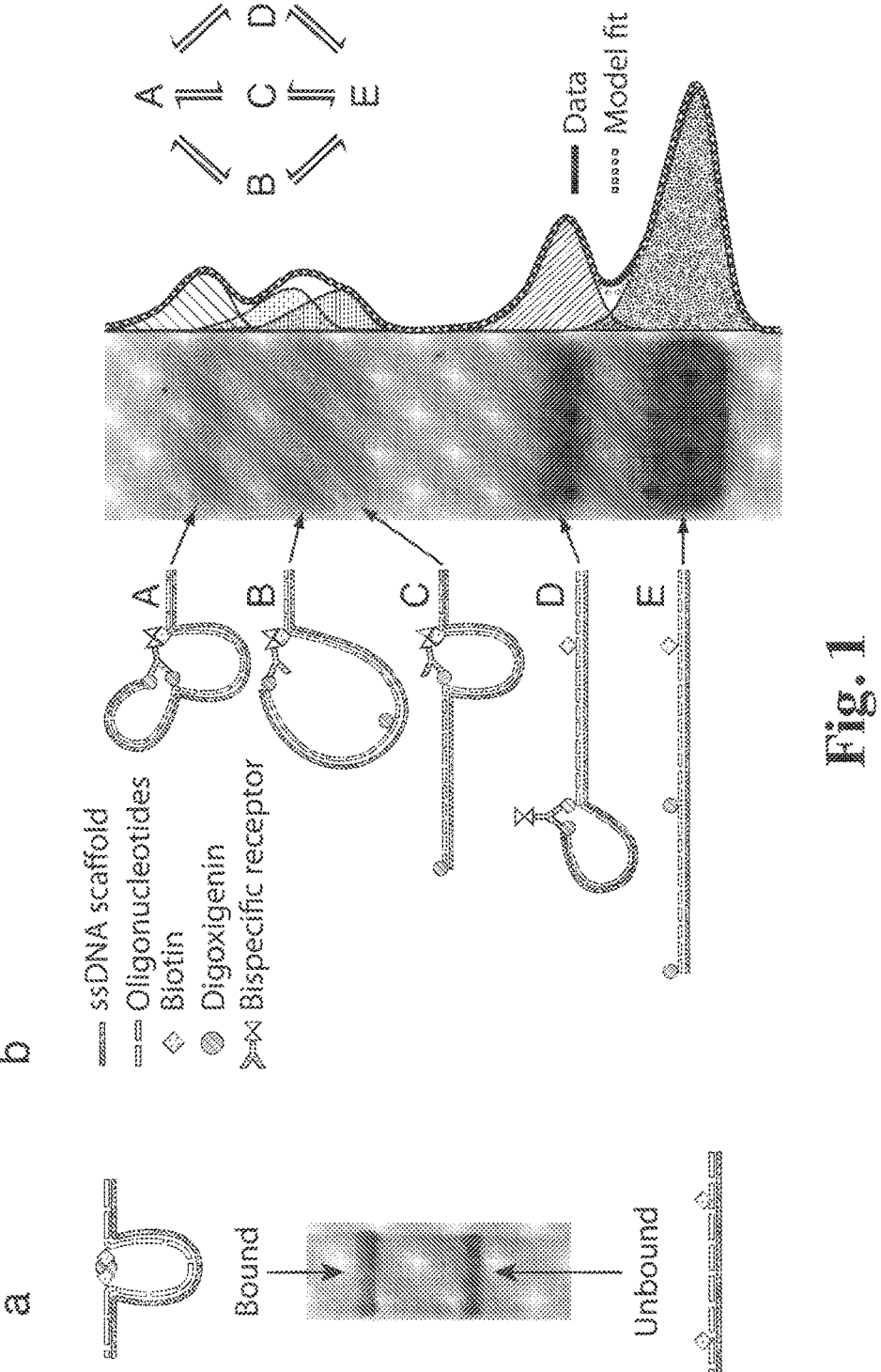
FIG. 1: DNA nanoswitches: a quantitative platform for gel-based biomolecular interaction analysis. (a) The two states (bound and unbound) of the DNA nanoswitches can be distinguished by gel electrophoresis. (b) A nanoswitch functionalized with two digoxigenin molecules and one biotin molecule can adopt five discernible states upon addition of a bispecific receptor. All five topological states, A-E can be resolved within a single lane of an agarose gel. Figure adapted from [ref. 2].

Provided herein are systems, compositions and methods for screening of a plurality of compounds, such as library members, and identification of compounds of interest. The systems, compositions and methods utilize nucleic acid complexes, also referred to herein as DNA nanoswitches, and nucleic acid barcoded compound libraries. As described in greater detail herein, nucleic acid complexes are molecular reagents that can hold multiple, potentially interacting, substituents on a nucleic acid scaffold (or backbone), and that change their geometry (e.g., shape, conformation, compactness, etc.) based on the interactions between such substituents. Such changes in geometry indicate the presence or absence of interactions between the substituents on the scaffold as well as other components in an assay system [ref. 1, 2]. Nucleic acid complexes can be used to perform kinetic and equilibrium measurements of a wide range of molecular interactions in solution using a gel electrophoresis readout (FIG. 1). By combining this technology with libraries of compounds that are barcoded with nucleic acids (e.g., DNA), it is possible to test simultaneously many different compounds for their abilities to interact with and modify the interactions of targets or binding pairs of interest in single reaction pools. Physical separation of different conformations of the nucleic acid complexes (also referred to herein as different interacting states) on a gel allows purification of such complexes, and subsequent high-throughput sequencing or multiple rounds of selection.

The methods provided herein facilitate high-throughput, logic-gated screening of compounds having a variety of activities. For example, the methods can be used to screen for and identify compounds that 1) affect the interaction(s) between two or more targets which may or may not bind to each other in the absence of the compound, and/or 2) modulate the allosteric state of one or more targets such as target proteins, and/or 3) specifically bind to a target such as a target protein, potentially even in the presence of decoy such as a mutant protein, and/or 4) bind multiple targets together, and/or 5) selectively modulate a specific target-to-ligand interaction.

This list is not intended as limiting the uses of the methods and compositions provided herein.

As described in the Examples, several proof-of principle experiments have been conducted using a variety of prototype systems relating to the foregoing screens. These include use of beta-2-adrenergic receptor. Src family kinases, and biotin-streptavidin binding pair.

The compounds to be screened are referred to herein as "candidates" to infer that they may possess the assayed activity. Compounds that have the assayed activity will cause the nucleic acid complex to adopt a particular structural conformation that will in turn have a particular migration rate through a gel. Compounds that do not have the assayed activity will not change the structure of the complex nor the migration rate of the complex through a gel.

The compounds may derive from a library although they are not so limited. The compounds may be drugs that are being screened for their binding and optionally allosteric activity, as described herein. Accordingly, the methods of the disclosure may be regarded as drug screening methods. It will be understood that the candidates may be of varied nature, including nucleic acids, peptides or proteins, a combination of nucleic acids and encoded proteins (such as for example, mRNA display nanobodies), small molecules including small synthetic molecules, and the like.

Significantly, the compounds being screened comprise a nucleic acid barcode. The barcode on each compound being tested is different from the barcodes on all other compounds being tested, and thus the barcodes are referred to as distinct or unique barcodes.

The barcodes may be part of the compounds naturally. For example, if the compound is a nucleic acid such as an aptamer, then the barcode may be part of or all of the aptamer sequence. Thus, if the library is a library of aptamers, it may not be necessary to label the compounds with barcodes as they may already be barcoded. Alternatively, aptamers may be conjugated to barcodes such that the putative target binding region is not the barcode.

The barcodes may be conjugated to the compounds during or post-synthesis. For example, if the compound is a peptide, protein or chemical compound, then it will be modified to include a nucleic acid based barcode.

The disclosure contemplates the use of existing barcoded libraries such as but not limited to aptamer libraries, small molecular DNA-barcoded libraries (e.g. X-Chem Pharmaceuticals), DNA-templated macrocycle libraries [ref. 3], and mRNA-display nanobody libraries. In addition, we can use this method to screen non-barcoded libraries by performing the looping reaction and analysis in separate reaction volumes.

As described in greater detail herein, compounds can be screened for their ability to allosterically modulate a target, thereby rendering the target more or less capable of binding to a known ligand. Compounds can be screened for their ability to bind specifically to a target of interest using nucleic acid complexes that are conjugated to the target of interest but also to structurally similar decoys, such as related family members of the target. In this way, the compound is screened for its ability to bind to the target of interest preferentially. The ability of the compound to bind specifically to the target of interest and interfere with target binding to a ligand of interest can be assayed using the same approach. Nucleic acid complexes used in these assays may be conjugated to the target of interest, the decoy, the ligand for the target of interest, the ligand for the decoy, and optionally the compound itself. As will be apparent based on this disclosure, various binding interactions may result in the presence of the compound including (1) target bound to its ligand and decoy bound to its ligand, indicating that the compound has no effect on either the target or the decoy;

(2) target not bound to its ligand and decoy bound to its ligand, indicating that the compound affects binding of the target to its ligand only;

(3) target bound to its ligand and decoy not bound to its ligand, indicating that the compound affects binding of the decoy to its ligand only;

(4) target not bound to its ligand and decoy not bound to its ligand, indicating that the compound affects binding of the target and the decoy to their respective ligands.

The aforementioned example provides readouts that may be observed whether the compound is conjugated to the complex or free in solution.

The disclosure provides nucleic acid complexes that are conjugated to the library compounds as well as various other substituents of interest. The disclosure alternatively provides nucleic acid complexes that are not conjugated to the library compounds. These latter complexes are used together with library compounds in solution, and the library compounds may be covalently conjugated to the complex, for example via a substituent conjugated to the complex, in order to retain the compound through the gel electrophoresis step.

Candidate Ligands/Library Compounds

Examples of barcoded libraries to be used in the methods of this disclosure are nucleic acid aptamer libraries, nucleic acid-encoded macrocycle libraries [ref. 3], and mRNA-displayed nanobody libraries.

Aptamers

The disclosure contemplates use of nucleic acid complexes to screen aptamers. The designed aptamers consist of multiple regions, including the region with variable sequence for which aptamer function will be screened for, constant regions that flank this variable region, a region or sequence that is complementary to a region of the scaffold of the nucleic acid complex (for conjugation to the complex), and an amine modification at the 3' end of the oligonucleotide that allows the aptamer oligonucleotide to be crosslinked to its target. Aptamers can be crosslinked to the targets to which they bind in order to preserve such binding even through the gel electrophoresis step. This may be particularly relevant if the aptamer is only weakly bound to the target. The constant regions that flank the aptamer sequence allow for multiple rounds of selection through purification and PCR. For multiple rounds of selection, single stranded DNA aptamers can be created from double-stranded PCR products by labeling the primer for the opposite strand with a 5' phosphate, and digesting the products with lambda exonuclease. Here the primers would cover the entire regions of the aptamer surrounding the central variable region, and the primer for the aptamer strand can also include a 5' amine group for cross-linking. The constant flanking regions can also be used to attached adapters for high-throughput sequencing around the variable region via PCR.

Figure 2:
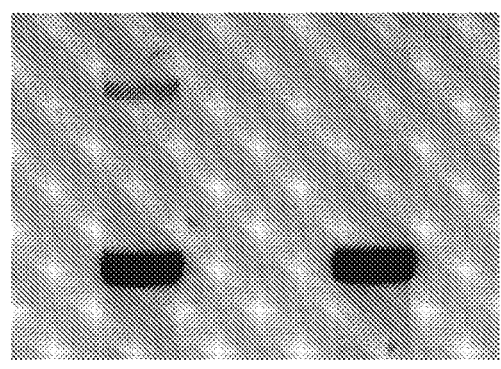
FIG. 2: Detection of aptamer binding using DNA nanoswitches. Looping is detected when a known aptamer sequences that binds to streptavidin is attached to the nanoswitch (left), but not in the case of a control sequence that does not bind Streptavidin (right). Here, glutaraldehyde is used to fix loops before gel electrophoresis

As a proof of concept, a DNA aptamer specific for streptavidin [ref. 8] was adapted in the foregoing manner, and it was conjugated to a nucleic acid complex that was also conjugated to streptavidin. We prepared the nano-switches by cooling a mixture of the aptamer, a biotin-modified oligonucleotide, the M13 scaffold, and tiling oligonucleotides from 90° C. down to 20° C. by one degree per minute. This mixture when then diluted to ~100 pM, and streptavidin was added to the mixture to bind to the biotin-modified oligonucleotide on the scaffold. After incubating at 30 minutes at room temperature, glutaraldehyde was added to cross-link for 45 minutes, and then the mixture was run on a 0.7% agarose gel pre-stained with SYBR-gold. The complex was observed to form a looped conformation when the streptavidin-specific aptamer was conjugated to the complex but not when a control aptamer sequence was conjugated to the complex (FIG. 2). Here, the control aptamer region is a sequence devoid of secondary structure.

Since the aptamer is nucleic acid in nature, the target-specific binding region of the aptamer, in whole or in part, may be used as the barcode.

The disclosure contemplates a system that evolves selected aptamers through repeated rounds of amplification by error-prone PCR. Thus after an aptamer is selected using the methods provided herein, it can be amplified in manner that will introduce mutation into its sequence, and the resultant variants can be screened themselves for their activity in the binding assays described herein (and from which the parent aptamer was identified).

Macrocycles

The disclosure further contemplates use of nucleic acid complexes to screen nucleic acid labeled macrocycles [ref. 3]. The nucleic acid labels on the macrocycle library members comprise three 6-basepair variable codon regions interspersed between regions of constant sequence. The variable region is different for each library member while the constant regions are common to all library members. The disclosure contemplates the use of a bridge oligonucleotide having a first region that hybridizes to the scaffold and a second region that hybridizes to the nucleic acid label of the macrocycle library member. The bridge oligonucleotide will capture all members of the macrocycle library. The second region of the bridge oligonucleotide comprises sequence that is complementary to the constant sequences that are common to all the macrocycle library members. The second region also contains stretches of deoxyinosine nucleotides that are able to pair with the variable sequences in the macrocycle label due to the ability of deoxyinosine to bind indiscriminately to A, C, G and T nucleotide bases.

To prevent bias in macrocycle library member binding to the nucleic acid complex, for example due to deoxyinosine having varying affinities for the four nucleotide bases, stoichiometric amounts of the bridge oligonucleotide and the library compounds are mixed during complex formation.

For downstream sequencing analysis, the nucleic acid tag of the macrocycle with its interspersed variable regions can serve as the barcode.

Figure 3:
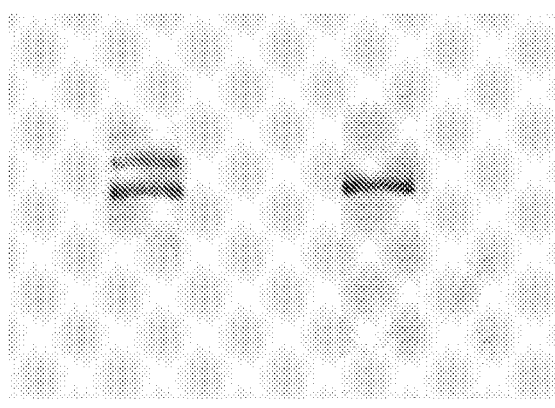
FIG. 3: Capture of macrocycle library sequence tag using a bridge oligonucleotide. Looping is detected when a biotinylated oligonucleotide that is identical in sequence to a macrocycle library member and our designed bridge oligonucleotide are hybridized to the scaffold and Streptavidin is added (left), but not in the case of a control sequence when Streptavidin is not added (right).
Figure 4:
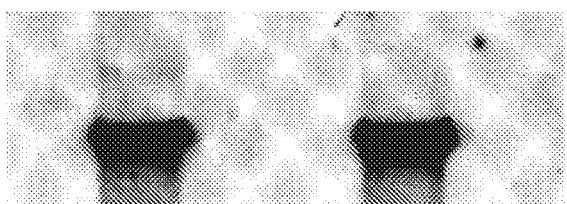
FIG. 4: Detection of insulin-degrading enzyme (IDE) binding to a DNA-encoded macrocycle using nanoswitches. Looping is detected when the macrocycle included (left), but not in the case of a control without the macrocycle (right). An oligonucleotide was attached to IDE using amine-reactive chemistry. The DNA-encoded macrocycle is captured using a bridge oligonucleotide.

A bridge oligonucleotide having these properties was produced and used to capture a biotinylated oligonucleotide identical in sequence to a macrocycle library member, and form looped conformations of a complex also conjugated to streptavidin (FIG. 3). The bridge oligonucleotide can also include an amino-modified Y end in order to crosslink the loop closed to detect weakly binding compounds. Amine-modified oligonucleotides can also be hybridized adjacent to the bridge and target protein to facilitate cross-linking. We have detected binding of insulin degrading enzyme to a macrocycle [ref. 7] using a nanoswitch (FIG. 4). Here insulin-degrading enzyme was attached to an oligonucleotide using non-specific amine reactive chemistry. Specifically, we reacted equimolar amounts of bifunctional DBCO-PEG4-N-hydroxysuccinimidyl ester (Sigma) with protein, then reacted with excess azide functionalized oligonucleotide (IDT), and then purified the protein using Ni Sepharose anti-His beads. The macrocycle was added to the nanoswitch by including the bridge and macrocycle along with the M13 scaffold and tiling oligonucleotides, and hybridizing via decreasing the temperature of the mixture one degree per minute, starting at 90 C and cooling to 20° C. The IDE-oligonucleotide complex was added to the hybridization mixture at 35° C. To detect looping, the hybridization mixture was diluted to a scaffold concentration of ~100 pM, incubated at room temperature for 30 minutes, cross-linked for 45 minutes, and then ran on a 0.7% agarose gel pre-stained with SYBR-gold.

The nucleic acid tag of the macrocycle with its interspersed variable regions can serve as the barcode.

mRNA-Display Proteins or Peptides (Nanobodies)

Figure 5:
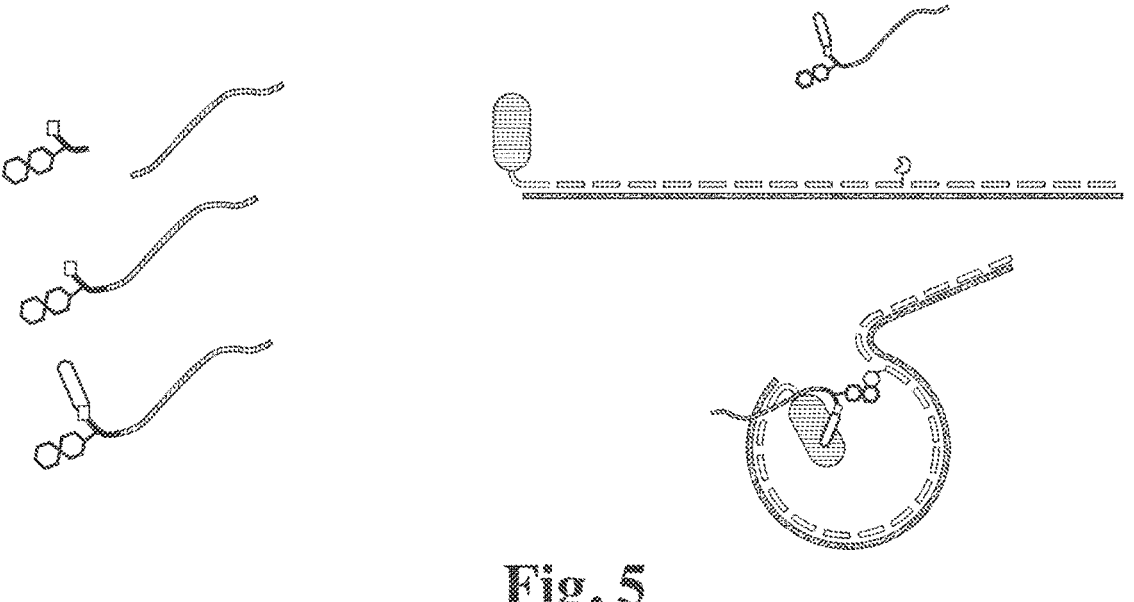
FIG. 5: Adaptation of mRNA to DNA nanoswitches. (left) A puromycin linker with a modified base containing a methyl-tetrazine is ligated to an mRNA molecule before translation, in order to create a mRNA displayed nanobody. (right) The mRNA displayed nanobody is attached to a nanoswitch that contains a Trans-Cyclooctene modified base.

The disclosure further contemplates use of mRNA-display peptides or proteins. mRNA-display is a technique that uses a puromycin linker attached to the 3' end of mRNA molecules to covalently attach the translated protein or peptide to the coding mRNA. In the context of this disclosure, the linker attached to the 3' end of the mRNA molecules may be further modified to include a modified deoxy-thymine nucleotide having a methyl-tetrazine attached thereto in addition to the 3' terminal puromycin. The corresponding scaffold is also modified to include a trans-cy-clooctene modification. When the mRNA-displayed peptide or protein is contacted with a scaffold containing the trans-cyclooctene modification, the displayed peptide or protein will covalently "click" onto the scaffold in a favorable and rapid cycloaddition reaction. This design allows the pre-construction of scaffolds and complexes for quick attachment to mRNA displayed peptides or proteins (FIG. 5).

The mRNA sequence of the library compound, in whole or in part, can serve as the barcode.

Isolation and Physical Separation of Library Compounds

When used with the nucleic acid complexes of the disclosure, the library compounds having desirable binding activities can be physically separated from other nucleic acid complexes using, in some embodiments, gel electrophoresis. As will be clear based on this disclosure, for each nucleic acid complex, the end user will determine a priori which conformations are possible and the migration distance of each conformation. Thus, once the library members are contacted with the nucleic acid complexes, the mixture is run through a gel, and regions of the gel are extracted and further analyzed based on the expected migration of each conformation. Barcodes contained in those extracted gel regions may be purified, amplified and/or sequenced in order to determine their identity and thus the identity of the library compound. In addition to sequencing, physical separation allows an end user to perform multiple rounds of selection, potentially in conjunction with error-prone PCR or other in vitro evolution techniques. The disclosure contemplates that other separation techniques could also be used including but not limited to capillary electrophoresis, and HPLC.

We have already successfully purified and sequenced aptamer sequences purified from an agarose gel, using both the Qiagen gel extraction kit and electroelution. Sanger sequencing of the extracted material after 25 rounds of amplification using Q5 polymerase (NEB) resulted in the expected sequence. Additionally, when we have run mixed aptamer and control sequences on a gel and extracted only the looped band corresponding binding events, we have >40 times enrichment of the aptamer sequence over the control sequence. This was shown using qPCR (SsoAdvanced™ Universal SYBR® Green Supermix) with aptamer-specific and control sequence-specific primer sets.

The methods provided herein may be viewed as a positive selection step that allows the physical separation of the complexes and library members of interest from the complexes and library members that are not of interest. This significantly increases the efficiency of the screening process.

In addition, as described herein, once isolated based on its binding profile, as provided herein, a candidate target-specific ligand such as an aptamer may be amplified using an error-prone enzyme such that variants of the isolated ligand are generated. Such mutants can then be screened using the same methods that identified the initial ligand. It will be understood that this can be accomplished with a single isolated ligand or a plurality of isolated ligands. The end result is an in vitro evolutionary process that allows an end user to generate and identify an optimal ligand which may not be part of the original source library.

Applications

High-Throughput Screening Assay for Allosteric Modulators

The disclosure provides an approach for the high-throughput screening of allosteric modulators by conjugating bar-coded library members to nucleic acid complexes that are themselves conjugated to target proteins of interest. This allows for the identification of library members that disrupt or enhance particular binding pair interactions such as receptor-ligand interactions.

Figure 6:
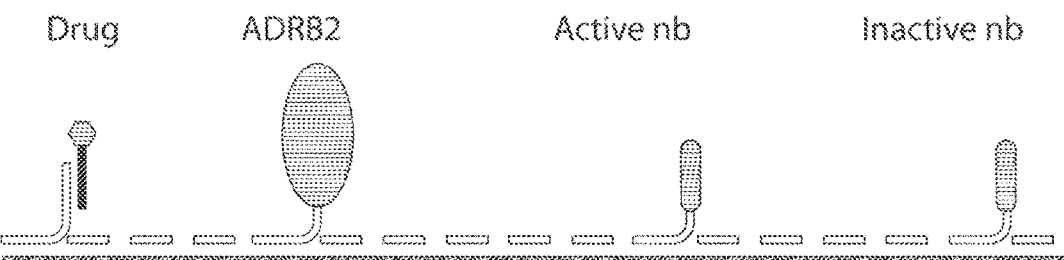
FIG. 6: Nanoswitch design for detection of allosterically modifying compounds for ADRB2 using state-specific binding nanobodies.

As a proof of principle, β2-adrenoreceptor (β2AR) is used as a model allosteric protein. This protein holds great importance as a drug target. The allosteric state of β2AR can be detected through its binding to nanobodies specific to the active or inactive state [ref. 5] or other binding partners that are specific for active or inactive states of a target. The nucleic acid complexes used in this application may comprise the β2-adrenoreceptor, nanobodies specific to the active and inactive states of β2AR, and also a potential drug from one of the previously described chemical libraries (FIG. 6)

Figure 7:
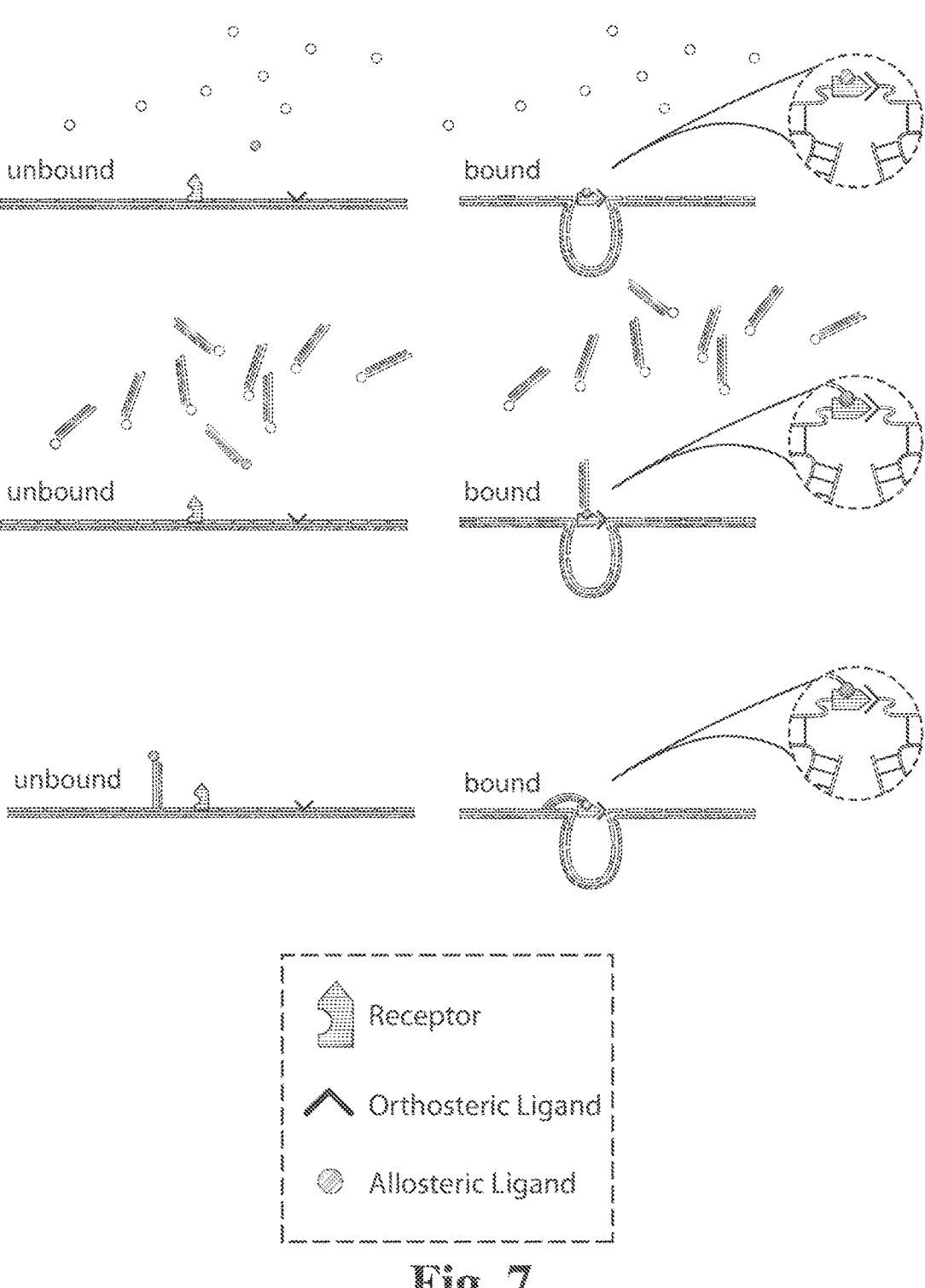
FIG. 7: Depiction of three distinct allosteric modulator screening assays based on DNA nanoswitch constructs. (top) V1: Testing one potential allosteric modulator at a time by observing changes in the receptor-orthosteric ligand binding kinetics in the presence of the potential allosteric ligand.

Compounds that can alter the allosteric state of a receptor can be identified by observing a shift in the binding equilibrium between the receptor and the two state-specific nanobodies or direct observation of concurrent binding of both the compound and nanobodies with the receptor. This method also works when only the ligand specific to the receptor of interest is attached to the nucleic acid complex instead of nanobodies specific to the active or inactive states. Similarly, in this case, allosteric compounds can be identified by concurrent binding of the compounds and ligand to the receptor (FIG. 7), or by observing the concentration-dependent modulation of the on-rate and/or off-rates between the ligand and receptor. In this and other aspects described herein, tethering the library member or compound to the scaffold is useful for finding compounds that have low affinity for the target since the DNA tether will keep the local concentration of the compound near the target high, and will also enable the allosteric compound to be extracted and identified even when it is not bound to the receptor, in the event it is not crosslinked to the target after binding thereto.

Protein based targets and ligands can be attached to oligonucleotides using sortase-tagging technology, such as that described in published PCT application WO2015/006626 and in the Examples. The sortase-tagging technology allows DNA to be covalently coupled to proteins at a specific site with minimal disturbance to protein function [ref. 5]. This can be accomplished using a two-step process. First, a small synthetic peptide is bioorthogonally and covalently coupled to a DNA oligonucleotide using click chemistry. Next, the DNA-peptide chimera is covalently linked to a protein of interest under protein-compatible conditions using the enzyme sortase. This protocol allows for the simple coupling and purification of a functional DNA-protein hybrid. In this way, sortase-tagged nanobodies can be conjugated to oligonucleotides complementary to the scaffold of the complex. The complexes constructed in this manner will be used to screen a library of drug compounds for their ability to allosterically inhibit or activate a target. As a proof of principle, we have selectively used nano-switches to detect activation of β2AR with the known high-affinity allosterically-activating compound BI167107, without any looping for the known high-affinity inactivating compound ICI118,551 (FIG. 8).

In addition to screening for compounds that affect the allosteric state of a protein and its ability to bind to an inactive or active-specific nanobody, this technique can also be used to screen for compounds that alter the state of a protein to bind to different ligands. An example of this would be to screen for compounds that alter the propensity of insulin degrading enzyme to bind to either insulin or glucagon.

Nucleic acid complexes can be used to screen for compounds that specifically bind to and inhibit a target such as a target protein, without affecting other moieties that are similar in structure to the target of interest. In these embodiments, the nucleic acid complex will comprise a member of the compound library, the target such as the target protein, and a decoy that is similar in structure but not identical to the target. Compounds of interest will create loops with the target, but not with the decoy.

As a proof-of-principle, libraries arm screened for compounds that specifically bind to Src, but not to other Src family kinases (FIG. 9). Loop formation between Src and a known Src-binding macrocycle [ref. 6] are then tested.

In addition, it is possible to screen for compounds that specifically inhibit mutant forms of Src present in cancer, while not inhibiting the wildtype Src. This screening approach will be general and applicable to other forms of oncogenic proteins.

Nucleic Acid Complexes (Also Referred to Herein as Nano-switches)

The disclosure provides nucleic acid complexes, also referred to herein as nanoswitches, for use in identifying binding interactions between known and/or unknown moiety. As will be described in greater detail herein, known moieties may be for example known binding pairs such as a receptor and its ligand. Unknown moieties may be for example members of a library such as a peptide library, a nucleic acid library, a small chemical compound library, a macrocycle library, an mRNA-display library, and the like. Typically, the identity of library members, including those of interest, is not known to the end user. The methods provided herein may be used to isolate library members of interest, by virtue of their ability to bind and optionally allosterically modify a target of interest, and then to identify such library members. Identification of the library member may include determining its chemical composition, including for example its nucleotide sequence or its amino acid sequence.

As also described in greater detail herein, each library member comprises (whether inherently or through conjugation post-synthesis) a distinct or unique nucleic acid barcode. This intends that each library member will be uniquely labeled with a barcode, and the barcode can be used to identify the library member with which it is associated, either inherently or through conjugation.

The nucleic acid complexes are modular complexes to which can be attached one or more targets of interest, one or more binding pairs of interest, one or more members of a protein family that may be similar but not identical to each other, moieties having different binding affinities for active or inactive states of a target of interest, and the like.

The terms attach, link and conjugate are used interchangeably throughout this disclosure unless otherwise stated.

The disclosure contemplates nucleic acid complexes that can be made using nucleic acid nanostructural techniques such as but not limited to DNA origami. (Rothemund P. W. K. (2006) Nature 440: 297-302; Douglas S. M. et al. (2009) Nature 459: 414-8).

In some aspects, the nucleic acid complexes are each comprised of a single "scaffold" nucleic acid and a plurality of oligonucleotides hybridized thereto. The scaffold nucleic acid and the oligonucleotides are single-stranded prior to hybridization to each other. Accordingly, the scaffold nucleic acid and the oligonucleotides may be referred to herein as being "single-stranded" and it is to be understood that this refers to their state prior to such hybridization.

This disclosure contemplates other forms of nucleic acid complexes as well as other ways of making such complexes.

In some embodiments, the nucleic acid complexes minimally comprise a nucleic acid to which one or more moieties are attached, either covalently or non-covalently. In some instances, the nucleic acid is a single stranded nucleic acid, and it may be referred to as the backbone or scaffold nucleic acid. Such backbone or scaffold nucleic acid may be hybridized to one or more (e.g., 2, 3, 4, 5, 6, 7, 8, 9, 10, or more) oligonucleotides. When more than one oligonucleotide is hybridized to the scaffold, such number of oligonucleotides is referred to as a plurality of oligonucleotides. Thus, a plurality of oligonucleotides intends 2 or more oligonucleotides. The number of oligonucleotides hybridized to the scaffold nucleic acid may be the same as the number of moieties attached to the scaffold nucleic acid, with each oligonucleotide itself attached to one moiety. In some instances, the number of oligonucleotides hybridized to the scaffold nucleic acid may be more than the number of moieties attached to the scaffold nucleic acid, with one or more oligonucleotides not attached to any moieties.

In some non-limiting embodiments, the nucleic acid complexes are formed by hybridizing a scaffold nucleic acid to one or more oligonucleotides. The disclosure contemplates any variety of means and methods for generating the nucleic acid complexes described herein. It is also to be understood that while for the sake of brevity the disclosure refers to oligonucleotides that are hybridized to a scaffold nucleic acid, such a complex may have been formed by hybridizing single stranded scaffold to single stranded oligonucleotides, but it is not intended that it was exclusively formed in this manner. Other ways of generating nucleic acid complexes having the same structure can be used and are contemplated by this disclosure.

The complexes of the invention may comprise double-stranded and single-stranded regions. Double-stranded regions may comprise "single-stranded nicks" as the hybridized oligonucleotides are not ligated to each other. The single-stranded regions are scaffold sequences that are not hybridized to oligonucleotides. Certain complexes may comprise one or more single-stranded regions in between double-stranded regions.

The scaffold nucleic acid may be of any length sufficient to allow association (i.e., binding) and dissociation (i.e., unbinding) of binding partners to occur and to be distinguished from other association and/or dissociation events using the read out methods provided herein, including gel electrophoresis.

In some instances, the scaffold nucleic acid is at least 1000 nucleotides in length, and it may be as long as 20,000 nucleotides in length (or it may be longer). The scaffold nucleic acid may therefore be 1000-20,000 nucleotides in length, 2000-15,000 nucleotides in length, 5000-12,000 in length, or any range therebetween. In some embodiments, the scaffold ranges in length from about 5,000-10,000 nucleotides, and may be about 7250 nucleotides in length.

The scaffold may be a naturally occurring nucleic acid (e.g., M13 scaffolds such as M13mp18). M13 scaffolds are disclosed by Rothemund 2006 Nature 440:297-302, the teachings of which are incorporated by reference herein. Such scaffolds are about 7249 nucleotides in length.

The scaffold nucleic acid may also be non-naturally occurring nucleic acids such as polymerase chain reaction (PCR)-generated nucleic acids, rolling circle amplification (RCA)-generated nucleic acids, etc. It is important that the scaffold nucleic acid is rendered single-stranded either during or post synthesis. Methods for generating a single-stranded scaffold include asymmetric PCR. Alternatively, double-stranded nucleic acids may be subjected to strand separation techniques in order to obtain the single-stranded scaffold nucleic acids. The scaffold nucleic acid may comprise DNA. RNA, DNA analogs, RNA analogs, or a combination thereof, provided it is able to hybridize in a sequence-specific and non-overlapping manner to the oligonucleotides. In some instances, the scaffold nucleic acid is a DNA.

In some instances, the scaffold nucleic acid is hybridized to a plurality of oligonucleotides. Each of the plurality of oligonucleotides is able to hybridize to the scaffold nucleic acid in a sequence-specific and non-overlapping manner (i.e., each oligonucleotide hybridizes to a distinct sequence in the scaffold).

The length and the number of oligonucleotides used may vary. In some instances, the length and sequence of the oligonucleotides is chosen so that each oligonucleotide is bound to the scaffold nucleic acid at a similar strength. This is important if a single condition is used to hybridize a plurality of oligonucleotides to the scaffold nucleic acid. In some instances, the oligonucleotides are designed to be of approximately equal length. The oligonucleotides may be, without limitation, about 40, about 50, about 60, about 70, about 80, about 90 or about 100 nucleotides in length. The number of oligonucleotides in the plurality may be 2, 3, 4, 5, 6, 7, 8, 9, 10, about 10, about 20, about 30, about 40, about 50, or about 60, or any range therebetween of the recited lengths without limitation. The number of oligonucleotides in the plurality may be about 70, about 80, about 90, about 100, about 110, about 120, about 130, about 140, about 150, about 160, about 170, about 180, about 190, or about 200, or any range therebetween of the recited lengths without limitation.

In some embodiments and as described in the Examples, the nucleic acid complex may comprise the M13 ssDNA as the scaffold and 120 oligonucleotides each equal to or about 60 nucleotides in length.

In some instances the first and last oligonucleotides as well as certain "internal" oligonucleotides may be interchanged with other oligonucleotides or may be modified oligonucleotides. These oligonucleotides may be referred to herein as "variable" oligonucleotides. The remaining unmodified oligonucleotides may be referred to herein as "backbone" oligonucleotides. The position of these variable oligonucleotides may be evenly distributed along the length of the scaffold.

As will be apparent in the context of this disclosure, the location of the variable oligonucleotides dictates the location of the various substituents in the complex, such as library members, targets, decoys, binding partners, binding pairs, etc. It also dictates the size of the loops that are formed once the various substituents bind to each other, as shown in FIG. 1. This will in turn dictate the migration distance of the complex, and thus the ability of the end user to physically separate and thus distinguish between complexes of interest and those not of interest.

FIG. 1 illustrates an exemplary nucleic acid complex functionalized with two digoxigenin molecules and one biotin molecule. The complex can adopt 5 discernable states upon addition of a bispecific receptor. All 5 topological states, A-E, can be resolved within a single lane of an agarose gel. These bands can be fit globally with a single fit of a sum of skewed Gaussian curves. The black curve represents the median pixel intensity, the dashed red curve represents the fit which is the sum of 5 skewed Gaussians. and the individual skewed Gaussians are shaded by state. The Figure also illustrates a reaction diagram illustrating the possible transitions between each of the 5 states. As described by Koussa et al., Nature Methods. Online publication Dec. 8, 2014 "DNA Nanoswitches: A Quantitative Platform for Gel-Based Biomolecular Interaction Analysis", by analyzing the distribution and intensity of bands in an agarose gel at various times, it is possible to determine on-rate and off-rate kinetics and rate constants.

The method requires that the various conformations adopted by the nucleic acid complex be distinguishable from each other when run on a gel such as an agarose gel, as shown in FIG. 1. Thus, the position of each functionalized oligonucleotide is typically known and pre-determined as are the conformations that can be formed from the complex.

It has been demonstrated in accordance with the invention that the methods allow an end user to physically separate complexes from each other using gel electrophoresis and to isolate complexes of interest from such gels. Significantly, this can be accomplished even if there is no discernable hand on the gel (i.e., no band is visible by eye). Nevertheless, the approximate location of each of the potential conformations is known a priori and these locations can be excised from the gel and further worked up to isolate any complexes contained therein.

The methods provided herein are described in the context of screening for a single ligand such as a candidate target-specific ligand or a single type of binding event. However, it is intended and it is to be understood that the nucleic acid complexes and their methods of use may analyze and identify more than one ligand and/or more than one binding event per nucleic acid complex, as shown in FIG. 1. That is, each nucleic acid may be constructed to detect more than one binding particular binding event, including for example detecting binding of a candidate ligand to a target, or detecting binding a candidate ligand to a target and binding of the ligand-bound target to another moiety, such as but not limited to a second ligand or binding partner.

According to the invention, certain of the oligonucleotides hybridized to the scaffold nucleic acid will be unmodified. Unmodified oligonucleotides include oligonucleotides that are not linked to substituents such as targets, library members, binding partners, etc. The majority of oligonucleotides hybridized to a scaffold nucleic acid may be unmodified. Unmodified oligonucleotides may be referred to herein as "fixed" or "backbone" oligonucleotides.

Other oligonucleotides hybridized to the scaffold may be modified. Modified oligonucleotides are oligonucleotides that are modified in one or more ways. Such oligonucleotides may comprise a modified nucleotide, and/or may have a modification at the 5' and/or 3' end, and/or may be conjugated to a non-nucleic acid moiety such as for example a peptide, a protein, or a macrocycle. Modified oligonucleotides may be referred to herein as "variable" oligonucleotides since these oligonucleotides may be modified by linking to a variety of binding partners depending on the method of use. Modified oligonucleotides may also be referred to herein as functionalized oligonucleotides.

Regions of the complex that comprise scaffold hybridized to unmodified oligonucleotides may be referred to herein as "fixed" or backbone regions. Regions comprising scaffold hybridized to modified oligonucleotides may be referred to herein as "variable" regions.

The spacing of modified (or variable) oligonucleotides along the length of the scaffold nucleic acid may vary. In some embodiments, the nucleic acid complex may comprise three or four variable regions (e.g., three or four modified oligonucleotides). As an example, a nucleic acid complex may comprise modified oligonucleotides at one or both of its ends as well as two internal modified oligonucleotides. The modified oligonucleotides at the ends of the complex may be used to conjugate the oligonucleotide to a substituent. The modified oligonucleotides internal to the complex may be linked individually to members of a binding pair (e.g., each of the two oligonucleotides is linked to a member of the binding pair such that the complex comprises the binding pair, with each member of the pair on a different oligonucleotide). The internal modified oligonucleotides may be symmetrically or quasi-symmetrically located around the center of the linker. In other words, they may be positioned equi-distant from the center of the scaffold (or the complex). Alternatively, they may be evenly spaced along the length of the complex as described in the Examples.

The nucleic acid complex may be formed by first hybridizing unmodified oligonucleotides to the scaffold nucleic acid to form a nucleic acid complex intermediate, and then hybridizing modified oligonucleotides to the scaffold nucleic acid to form the nucleic acid complex. The modified oligonucleotides may be combined with (and typically hybridized to) the scaffold simultaneously or sequentially. As used herein, a nucleic acid complex intermediate refers to a scaffold that is hybridized to some but not the entire complement of oligonucleotides that is designed to bind to the entire length of the scaffold. In other embodiments, unmodified and modified oligonucleotides are combined with (and thus hybridized to) the scaffold simultaneously.

REFERENCES

1. Halvorsen K, Schaak D. Wong W P (2011). Nanoengineering a single-molecule mechanical switch using DNA self-assembly. Nanotechnology. 22(49):494005.
2. Koussa M A, Halvorsen K, Ward A. Wong W P. (2015) DNA nanoswitches: a quantitative platform for gel-based biomolecular interaction analysis. Nat Methods. 12(2): 123-126.
3. Gartner Z J, Tse B N, Grubina R, Doyon J B, Snyder T M, Liu D R (2004). DNA-templated organic synthesis and selection of a library of macrocycles. Science. 305(5690): 1601-1605.
4. Ring A M, Manglik A, Kruse A C, Enos M D, Weis W I, Garcia K C, Kobilka B K (2013). Adrenaline-activated structure of β2-adrenoceptor stabilized by an engineered nanobody. Nature. 502(7472):575-579.
5. Koussa M A. Sotomayor M, Wong W P (2014). Protocol for sortase-mediated construction of DNA-protein hybrids and functional nanostructures. Methods. 67(2): 134-141.
6. Georghiou G. Kleiner R E, Pulkoski-Gross M, Liu D R, Seeliger M A (2012) Highly specific, bisubstrate-competitive Src inhibitors from DNA-templated macrocycles. Nat Chem Biol. 8(4):366-74.

EXAMPLES

Example 1. DNA Nanoswitches: A Quantitative Platform for Gel-Based Biomolecular Interaction Analysis Abstract Provided herein is a nanoscale experimental platform that enables kinetic and equilibrium measurements of a wide range of molecular interactions by expanding the functionality of gel electrophoresis. Programmable, self-assembled DNA nanoswitches serve both as templates for positioning molecules, and as sensitive, quantitative reporters of molecular association and dissociation. We demonstrate this low cost, versatile, "lab-on-a-molecule" system by characterizing 10 different interactions, including a complex 4-body interaction with 5 discernable states.

Materials and Methods

General Nanoswitch Formation:

The nanoswitches were constructed as previously described in detail-. Circular-single-stranded DNA from the 7249 nt bacteriophage M13 (New England Biolabs) was linearized by enzymatic cleavage of a single site using BtscI (New England Biolabs) and a site specific oligonucleotide. Oligonucleotides (from Bioneer or Integrated DNA Technologies (IDT)) were designed to complement the linearized M13 DNA along the backbone, resulting in 120 60-nt oligonucleotides and a single 49 nt oligonucleotide. The first and last oligonucleotide along with 10 evenly distributed oligonucleotides are intended to be interchangeable and will be referred to as variable oligonucleotides (var 1-12, with var 1 representing the first oligonucleotide and var 12 representing the last oligonucleotide). These variable oligonucleotides were stored separately from the remaining 109, referred to as backbone (bb) oligonucleotides, which were mixed in equimolar concentration in a single tube. Mixing a molar excess of the oligonucleotides (10:1 unless otherwise noted) with the ssDNA scaffold and subjecting the mixture to a temperature ramp (90° C. to 20° C. at 1° C./minute unless otherwise noted) produced double stranded DNA. Final constructs were spiked with a low concentration of DNA ladder (BstNI Digest of pBR322 DNA, New England Biolabs) to aid in quantification. For many experiments the constructs were PEG precipitated after annealing to remove excess oligonucleotides. The PEG precipitation was performed as previously described in[16].

Design Considerations:

The nanoswitches were designed with several key design considerations to ensure that they function properly and robustly over a wide range of conditions. The oligonucleotide length was selected to be 60 nt to ensure both site specificity, and to ensure that the oligonucleotides would not spontaneously fall off even at temperatures as high as 50° C. We show that at 50° C. even a 20-mer oligonucleotide has a long lifetime of ~18 hours (data not shown), and the lifetime of a 60-mer oligonucleotide is predicted to be orders of magnitude longer than the 20-mer oligonucleotide[17].

The ligands were positioned at locations that allow for easy resolution of the looped and unlooped bands. Placement of the oligonucleotides on variable regions 4 and 5 yields two bands that are quite close to one another under our standard gel running conditions. The further apart the ligands are, the more easily resolvable the two bands become. The spacing of ligands on the DNA scaffold also controls their effective concentration, with the effective concentration of one ligand to the other generally decreasing as they are spaced further apart (though if the ligands are brought within one persistence length of the polymer, the effective concentration may decrease dramatically). We have found that the use of variable regions 4 and 8 provides a nice middle ground.

Regarding the concentrations, it is important to consider that there are three concentrations that can be independently tuned in an on-rate experiment. There is the concentration of the scaffold, the concentration of the receptor, and the effective concentration between the two ligands on the polymer. If these concentrations are adjusted carefully, many problems can be avoided. For example, if the effective concentration between the two tethered ligands is significantly higher than the concentration of the receptor, then one can minimize capping (the binding of two receptors to a single scaffold resulting in an unloopable construct). We note, however, that since our model accounts for capping, the values obtained outside this optimal regime will still be correct, the looped-band intensities will simply be weaker, resulting in a lower signal-to-noise. Although not usually a problem, one can avoid higher order aggregation by ensuring that the scaffold concentration is significantly lower than the effective concentration between the two ligands on the scaffold. One can also simplify the analysis by selecting a receptor concentration that is significantly higher than the scaffold concentration so that the receptor concentration stays effectively constant over the course of the experiment. Following these experimental design principles, in our experiments using variable oligonucleotides 4 and 8, the effective concentration between the two ligands on the loop is ~30 nM, the scaffolds are used at a concentration of 80 pM, and the receptor is used at a nominal concentration of 3 nM.

In addition to the ratio of concentrations there are some important lower and upper limits of concentration to keep in mind. We have found that working with protein concentrations below 1 nM can be unreliable due to losses of protein to the walls of the tubes. We have performed on-rate experiments with streptavidin concentrations as low as 0.3 nM but losses of protein can be as high as 80% even in protein LoBind tubes (Eppendorf technical data sheet). Unless a means of eliminating protein loss to tubes and pipette tips is implemented, we do not recommend working below 1 nM. The upper limit is not a hard limit. We have found that the on-rate for streptavidin is very fast at 30 nM, making it difficult to pipette fast enough to take multiple time points before the plateau. If one has a means of more rapidly mixing solutions (i.e. microfluidics), or a protein with a slower on rate, higher protein concentrations can be used. We have found that 3 nM provides a nice middle ground, though one may wish to optimize the protein concentration used based on the speed of mixing, and the solution on-rate of the protein being studied.

Following these design principles and those laid out in[5], is key to the successful use of this platform. To aid in implementing this method in your lab we have written a supplementary protocol (Appendix A) which provides information on reagents needed, and detailed step-by-step instructions on how to successfully perform on-rate and off-rate experiments.

Electrophoretic Conditions

All looped constructs were run in 0.7% agarose gels, cast from LE agarose (Seakem) or Ultrapure Agarose (Life Technologies) dissolved in 0.5× Tris-borate EDTA (TBE) (Biorad). Before loading, samples were mixed with a Ficoll-based loading solution (Promega), which we found to give sharper bands than glycerol-based loading dyes, simplifying quantification. Gels were run for 90-100 minutes at 4 V/cm, unless otherwise noted, and subsequently stained in 1× SYBRGold stain (Invitrogen) for a minimum of 30 minutes before being imaged with a gel imager (Biorad) or laser gel-scanner (GE Typhoon). It is important to note that the standard output file of this imager is often set to a gel file which has a non-linear intensity scaling. .gel images can be linearized using the imageJ Linearize gel Data plugin available at the rsb.infor.nih.gov/ij/plugins/linearize-gel-data website. Alternatively the gel image can be saved as a linear .tiff file off of the imager. These expensive imagers are not required for quantification; we obtained similar results using a blue transilluminator (Invitrogen) and a point and shoot camera (Canon S95).

Biotin-Streptavidin Nanoswitch Experiments

This construct used biotinylated versions of two oligonucleotides (var 4 and var 8), which were used in 4× molar excess to the scaffold, while all other oligonucleotides were used in a 10× molar excess. The reason for this lesser amount is twofold: 1) to be less wasteful of the more expensive functionalized oligonucleotides, and 2) because excess biotin oligonucleotide in solution could interfere with our measurements. The final DNA construct was then diluted 100× from its original concentration of ~16 nM (to 160 pM), and mixed in equal volumes with streptavidin (Rockland) at 6 nM nominal concentration to form the loops, yielding final nominal concentrations of ~80 pM and 3 nM, respectively.

On-rate experiments were performed by mixing equal volumes of 160 pM DNA construct with a nominal 6 nM streptavidin concentration, followed by taking 10 μL aliquots of the mixture at various times and mixing them with 1 μL of a saturated biotin solution to quench the formation of loops. The 25° C. experiment was performed at room temperature, the 4° C. experiment was performed in a cold room, and the 37° C. and 50° C. experiments were performed using a thermal cycler. It is important to note that for on-rate experiments, using low binding tubes (Eppendorf LoBind) was important for getting repeatable results due to significant streptavidin adsorption to the tubes when incubated at 6 nM. Actual concentrations used to determine the on-rates were measured using spectrophotometry and a HABA assay to determine streptavidin activity. We found that the actual streptavidin concentration was within 10% of the nominal concentration, and over 85% of the protein was active based on the HABA assay.

Off-rate measurements were performed by forming looped construct as described above, and letting the solution sit for at least 24 hours to allow the system to reach equilibrium. Aliquots of the looped construct were mixed at various times with a quenching solution consisting of biotin and sodium chloride to achieve the proper experimental salt concentrations, and immediately put at the experimental temperature. The 4° C. condition was done in a refrigerator, the 25° C. sample was done in a water bath, and the 37° C. and 50° C. temperatures were done in a thermal cycler. To run all the samples on a single gel, the quenching times were determined relative to the predetermined gel running time.

Preparations with avidin and neutravidin were prepared in the same way, but protein concentrations were sometimes altered to enable on-rate measurements over a similar time scale as the streptavidin experiments.

Desthiobiotin-Streptavidin

Desthiobiotin experiments were conducted in a similar manner as the biotin experiments with slight modifications. The var 4 oligonucleotide was changed to a desthiobiotin-functionalized oligonucleotide while the var 8 oligonucleotide remained biotin functionalized. The off-rate of the desthiobiotin interaction is much faster than the typical 100 minute gel run time. Noting that once a loop opens in the gel, the reptation of the DNA prevents the loop from closing again, we ran samples for different amounts of time in the gel at 15 V/cm and 4° C. and quantified the fraction looped as a function of running time (Appendix A—Supplementary FIG. 5). In addition to allowing the determination of the desthiobiotin-streptavidin off rate, this gel also allowed us to determine the minimum amount of time required to achieve separation of the looped and unlooped bands in the gel. This enabled the use of the standard quenching technique for measuring desthiobiotin off-rates as described in the previous section; these gels were run at 15 V/cm for 10 minutes in pre-chilled electrophoresis buffer.

DNA Hybridization Experiments

This construct used a 50 nt "bridge" oligonucleotide to span the last 30 nt of the var 4 region and the first 20 nt of the var 8 region. Thus, the normal var 4 and var 8 oligonucleotides were omitted from the mixture and replaced with 3 oligonucleotides: the aforementioned "bridge" oligonucleotide and two small "filler" oligonucleotides to fill the remaining bases so that the M13 scaffold would be fully hybridized. In this case, the bridge oligonucleotide was added in equimolar concentration with the scaffold strand, while the other oligonucleotides remained at 10× molar excess. Off-rate measurements were quenched with 500 nM 20 nt oligonucleotide corresponding to the loop closure site. Kinetics were accelerated by performing the measurement at 50° C.

Enzyme Cleavage Experiments

These constructs were made as described above, but with a bridge oligonucleotide containing an inserted sequence recognized by the XhoI enzyme (New England Biolabs). The compliment to this restriction sequence was also added to ensure that this region was double stranded. Cleavage measurements were performed by adding enzyme to the loops (with final concentrations of 2.2 nM and 1.000 units/ mL for the loops and enzyme, respectively) in the recommended buffer (New England Biolabs) and quenching the enzyme activity with 75 mM EDTA at various times at room temperature.

Antibody-Antigen Experiments

This construct used a 3' digoxigenin labeled version of the var 8 oligonucleotide (Integrated DNA Technologies) and a 5' anti-dig labeled version of the var 4 oligonucleotide. The antibody labeled oligonucleotide was made by chemically crosslinking a free amine on the antibody (Polyclonal Sheep Antibody from Roche) to a thiol labeled oligonucleotide, and purified by electroelution as described previously[5]. The construct was made with two annealing steps. First, all the oligonucleotides with the exception of the antibody-labeled oligonucleotide were mixed with the scaffold strand and annealed following our standard protocol described above (except a 1:1, rather than 10:1, molar ratio was used for the digoxigenin oligonucleotide). Second, the purified antibody oligonucleotide was added in a 1:1 molar ratio and annealed from 37° C. to 4° C. at 0.5° C./minute to facilitate annealing of the antibody-modified var 4 oligonucleotide. Off-rate measurements were performed by quenching with 335 nM of antibody at various times at room temperature.

Sortase Catalyzed Peptide Ligation experiments

This construct was created in 3 steps. 1) Var 4 and var 5 oligonucleotides with a 3' and a 5'azide respectively, were functionalized with sortase compatible peptides. 2) These two oligonucleotides were linked together with sortase. 3) The peptide-bridged oligonucleotides were hybridized onto the DNA nanoswitch. All custom peptides were purchased from NeobioLab.

1) To create the sortase-compatible oligonucleotides, sortase-compatible peptides were covalently attached using click chemistry as previously[16], the entire contents of which are incorporated by reference herein. Pra-LPETGHHHHHH, where Pra is a Propargyl glycine which adds an alkyne functionality (SEQ ID NO:1), was coupled to var 4-azide using copper-catalyzed click chemistry. Azide-var 5 was then functionalized with a Flag-TEV-GGG-Pra peptide (SEQ ID NO:2), where Flag denotes a Flag-tag and TEV denotes a cleavage site for the Tobaco etch virus protease. After the click chemistry the oligonucleotides were processed with a qiagen nucleotide removal kit and run on a polyacrylamide gel. The bands corresponding to the peptide-oligonucleotide chimeras were cut out and the products were extracted via electroelution as previously described.

2) Once purified the Flag-TEV-GGG-var 5 was treated with TEV (Sigma) and the two oligonucleotides were concentrated as previously[16]. These oligonucleotides were then at a concentration of ~10 uM as judged by running on a precast 4-20% gradient polyacrylamide TBE gel (BioRad). Equal volumes (10 μL each) of the sortase-compatible oligonucleotides were mixed with 5 μL of 14.1 mg/ml sortase (Chen et. al. 2011), and 25 μL of 2× Sortase Reaction buffer (600 mM Tris HCl pH 7.5, 300 mM NaCl, 10 mM MgCl₂, and 10 mM CaCl₂). This was allowed to sit for 3 hours at room temperature before running on a polyacrylamide gel and purifying the dimer band via electroelution. Yielding var 4-LPETGGG-var 5 (SEQ ID NO:3) (Note that the GGG indicates the amino acid string Gly-Gly-Gly.

3) The var 4-LPETGGG-var 5 (SEQ ID NO:3) was used instead of the normal var 4 and var 5. This was annealed onto the linear M13 backbone at a 1:1 ratio and was added along with the other oligonucleotides at the beginning of the annealing, as peptide denaturation was not a concern. This yielded loops with the peptide LPETGGG (SEQ ID NO:3) bridging variable regions 4 and 5.

With these loops in hand we could observe loop opening as a result of sortase ligating free GGG-X peptide. To accomplish this a mixture was made with the following concentrations. 2 nM DNA nanoswitches, 10 μM sortase, 40 μM GGG-S—S—CH₃, 300 mM Tris HCl pH 7.5, 150 mM NaCl, 5 mM CaCl₂, and 5 mM MgCl₂. Catalysis by sortase is highly calcium dependent thus the transpeptidation could be quenched at different times by adding an equal volume of 100 mM EDTA in water. 10 time points were collected over 20 minutes at room temperature.

Disulfide Reduction:

This construct was created in 3 steps. 1) Var 4 and a truncated version of var 8 with a 3' and a 5' thiol respectively, were reduced in 50 mM TCEP (BondBreaker Thermo Scientific). 2) These two oligonucleotides were linked by a disulfide. 3) The disulfide-bridged oligonucleotides were hybridized onto the DNA nanoswitch.

1) To reduce the thiols on the oligonucleotides they were incubated in 50 mM TCEP for 1 hour at RT.

2) Equal volumes of the two oligonucleotide-TCEP mixtures were then combined. The TCEP was removed using a QIAGEN nucleotide-removal kit. The oligonucleotides were then allowed to form disulfides in the absence of reducing agent in PBS for 1 hour before running the products on a precast 4-20% gradient polyacrylamide TBE gel. As the oligonucleotides were different sizes (60 and 30 nt) the appropriate hetero dimer could be easily identified and purified using electroelution as previously described[5].

3) The var 4-S—S-var 8 was used instead of the normal var 4 and var 8. This was annealed onto the linear M13 backbone at a 1:1 ratio and was added along with the other oligonucleotides at the beginning of the annealing. This yielded loops with a disulfide bridging variable regions 4 and 8.

With these loops in hand we could observe loop opening as a result of TCEP reduction of the disulfide bond. To accomplish this equal volumes of 20 μM TCEP and 160 nM loops, both of which were diluted in NEB buffer 2, were mixed at different time points before running the gel. 7 time points were collected over 10 days at room temperature before running the gel.

MultiState Loops

The bispecific receptor was formed by using a lightning link kit (Innova Biosciences) to attach streptavidin to sheep polyclonal antidig (Roche 11333089001). The antidig, suspended in PBS, was added in a 1:1 ratio to the streptavidin, and the kit protocol was followed exactly. This was then diluted 1:1250 into NEB Buffer 2 with added 150 mM NaCl before use in forming multistate loops. The multistate loop was formed by using var 4 with a 3' biotin, var 8 with a 5' digoxigenin, and var 12 with 3' digoxigenin in place of the normal var 4, 8, and 12 oligonucleotides. On-rate and off-rate measurements were performed using the same procedure used for the biotin-streptavidin experiments with slight modifications. Rather than adding streptavidin, the diluted bispecific receptor was added, samples were quenched with 2 μL of 5 μM digoxigenin-functionalized oligonucleotide (an oligonucleotide was used as digoxigenin is not water soluble) suspended in a saturated biotin solution. Gels were run 6.25 V/cm for 125 minutes with buffer chilled to 4° C. before running.

Gel Image Analysis

We analyzed gel images in one of two ways:

1) All non-multistate (only two bands) gels were analyzed in the following way:

The amount of material in each gel band was quantified by analyzing the scanned gel images with the gel analysis tool in the freely available ImageJ software package. Using rectangular regions of interest that just capture the width of the gel bands, this toolbox produces intensity profiles whose area can be measured to quantify the total brightness in each band. We applied the same rectangular window size to each lane within a single gel. In many gels the highest molecular weight band of the added ladder was used as a normalizing reference lane. This relaxed the constraints of pipetting perfectly across all lanes.

2) All multistate (with 5 bands) gels were analyzed as follows

A custom MATLAB interface was developed for fitting the intensity profiles of the imaged gel bands. The software interface was modeled after the Image) interface. Rectangular boxes are drawn around each lane to define a region of interest. Median filtering is a common technique used to remove speckle noise in images. Rather than filtering the entire image, each individual lane was median filtered by row to remove speckle noise without sacrificing resolution in the direction of band migration. After plotting the median-intensity profile the background was subtracted using a 4-6 point piece-wise linear function to outline the background. The background was found to be very similar across lanes and often the same background profile could be subtracted from the majority of the lanes. Once the profiles were extracted, least-squares fitting of each profile to the model was performed in MATLAB. Individual bands run on their own show a skewed Gaussian profile, also known as a skew normal distribution, with a skew parameter of ~–2.5 (data not shown). Thus, the entire multistate median-intensity profile (from just above the highest band to just below lowest) was fit using a sum of 5 skewed Gaussians. A common skew parameter was used for all 5 bands, and a common initial guess of band width was used with a fitting range of ±10 pixels. These input parameters allowed for converging fits across all lanes, and resulted in fits that closely matched the observed intensity profiles (data not shown). The areas of the individual bands were calculated by integrating the individual skewed Gaussians. Error in the fitted areas was estimated by calculating the areas within the one-sigma confidence interval of the lit parameters. These areas were all normalized by the total area (the sum of all of the skewed Gaussian areas). The identity of the bands were validated by analyzing gels in which individual loop sizes were formed (data not shown). Accuracy of band quantification was confirmed by mixing these individual loops in known ratios—the measured values of the individual bands were found to be within 10% of their true values.

Equation for a skew normal/skewed Gaussian distribution:

$$A \cdot e^{-\left(\frac{x-b}{c}\right)^2} \cdot \left(1 + \mathrm{erf}\left(a\frac{x-b}{c}\right)\right)$$

Data Analysis

Based on a gel we ran to establish repeatability of pipetting and imaging, we conservatively estimate the error per lane at ±5% plus the detection limit (which will vary by imager). For lanes that used a reference band to normalize brightness, the 5% error per band was propagated to yield roughly 7% error per measurement. Error bars were produced based on this analysis, and all fitting procedures used an error weighted least squares fit. Timed pipetting for on-rate experiments was conservatively assumed to have an error of 2 seconds, which was propagated to overall y-error by multiplying by the derivative of a preliminary fit.

Model

The time evolution of DNA nanoswitch states are modeled using multistep reaction kinetics.

On rates are modeled as a two-step process:

Unbound Linear→Singly Bound Linear→Looped

Step 1 represents the binding of a free receptor in solution to a ligand on the scaffold (yielding the solution on-rate). Step 2 represents the subsequent binding of this receptor to another ligand on the same scaffold to form a loop (yielding the loop-closure rate). On-rate and off-rate models for both the two-state and five-state systems are detailed in the supplementary discussion of Koussa et al. Nature Methods, 2014.

Thermodynamic Analysis

The dissociation constant $K_D$ was determined by the ratio of the off- and on-rates, and the equilibrium free energy $\Delta G^0$ was determined by:

$$\Delta G^0 = -RT \ln(\tilde{K}_D)$$

Where R is the gas constant, T is the absolute temperature, and the dissociation constant, which is determined by dividing the off rate by the on rate, and is made dimensionless by dividing it by a reference concentration, i.e. $\tilde{K}_D = K_D/(1M)$. We additionally used Eyring analysis to fit the temperature dependence of the kinetic rates:

$$\ln\left(\frac{k}{T}\right) = \frac{-\Delta H}{R}\left(\frac{1}{T}\right) + \ln\left(\frac{k_B}{h}\right) + \frac{\Delta S}{R}$$

Where k is the kinetic rate constant, $k_B$ is the Boltzman constant, h is Plank's constant, and $\Delta H$ and $\Delta S$ are the enthalpy and entropy of activation, respectively.

For the salt dependence, we used the kinetic salt relationship:

$$\log(k) = \log(k_0) + 2A \cdot Z_A \cdot Z_B \sqrt{I}$$

Where k is the kinetic rate constant, $k_0$ is the rate constant without the salt. A is the Debye-Hückel constant, $Z_A$ and $Z_B$ are the charges on the two interacting species, and I is the ionic strength of the solution.

Results and Discussion

Gel electrophoresis has been a workhorse of biological research for over 50 years, providing a simple way to determine size, topology, and quantity of DNA, RNA, and protein[1, 2, 3]. However, quantitative kinetic and thermodynamic characterization of molecular interactions on gels remains a challenge. For example, electrophoretic mobility shift assays (EMSA) are primarily used for qualitative analysis of protein-nucleic acid interactions[4]. Quantitative biomolecular interaction analysis typically requires specialized techniques such as Surface Plasmon Resonance (SPR) (e.g. Biacore), radiolabeling, or Isothermal Titration Calorimetry (ITC), with cost, required technical expertise, and material requirements sometimes posing barriers to their use (data not shown). Furthermore, quantitative analysis of long-lived interactions, small molecule interactions, and multicomponent complexes are difficult, even with these advanced approaches.

We introduce a new instrument-free platform, based on DNA self-assemblys[5, 6, 7], that meets these challenges by enabling quantitative analysis of molecular interactions using standard gel electrophoresis, for pennies per sample (data not shown). DNA oligonucleotides (60 nt) are functionalized with interacting molecules, and hybridized to specific locations on a single-stranded DNA scaffold (M13mp18, 7,249 nt). These DNA nanoswitches report molecular associations and dissociations through induced topological changes. Exploiting the ability to separate DNA based on topology[8], the different interaction states can be easily resolved as distinct bands on a gel (data not shown).

These nanoswitches have several important features. Their programmable nature enables precise control over relative concentrations and stoichiometries on a per molecule basis. The large DNA construct causes interaction-triggered topological changes to yield distinct and repeatable gel shifts, even with the integration of large proteins[5]. Additionally, the size of the DNA allows for the incorporation of thousands of dye molecules, dramatically amplifying the signal per interaction, and making readout of the nanoswitches orders of magnitude more sensitive than most other techniques (data not shown). Together, these features make this a versatile, accessible, and inexpensive tool for studying multi-molecular interactions.

By monitoring changes in the nanoswitch states over time, we can determine equilibrium and kinetic rate-constants for a variety of molecular systems using standard gel electrophoresis. Loop closure over time is used to determine association rate-constants, while loop opening over time, in the presence of a competitor, is used to determine the dissociation rate-constant (data not shown). These kinetic processes take place in solution and are "quenched" to halt kinetics at various time points, with the gel acting as a post-experiment readout, enabling experimental conditions that are independent of gel running conditions. Ease of readout and other nanoswitch characteristics can be optimized by tuning key design parameters, including oligonucleotide length, ligand positioning, reaction concentrations, and temperatures (online methods).

We first assessed the nanoswitch platform using the ubiquitous biotin-streptavidin system. At physiological salt conditions and 25° C., we measured a dissociation time of 9.7±0.4 days (all values are reported as the error-weighted fit parameter t its one-sigma confidence interval), closely matching previously reported values[9]. To demonstrate parallel exploration of a broad range of experimental conditions, we measured off-rates at 16 different conditions, by measuring the fraction dissociated at 6 time points per condition, and running all 96 samples on a single gel (data not shown). Each condition showed exponential decay over time, yielding 16 uniquely determined off-rates ranging from 0.8 hours to 3 months with an uncertainty typically less than 10% (data not shown). Dissociation kinetics varied nearly 1,000 fold over our temperature range (4-50° C.) but only about 2 fold over our salt range (25-500 mM) (data not shown). Based on these results, we present a semi-empirical model for dissociation kinetics between streptavidin and biotin-labeled oligonucleotides from 25° C. to 50° C. and 25 mM to 500 mM NaCl:

$$k_{off} \approx Te^{\left(42.4-\frac{18300}{T}-0.033\sqrt{I}\right)}$$

Where $k_{off}$ is the value of the off-rate in $s^{-1}$, T is the value of the absolute temperature in K, and I is the value of the ionic strength of the solution in mM (data not shown). This model does not describe the behavior at 4° C. presumably due to temperature dependent changes in heat capacity[10].

On-rate kinetics were measured, at a variety of temperatures, by monitoring loop formation over time. Loop closure occurs through two separate binding events, the binding of a molecule from solution to the nanoswitch, and then the closing of the loop. Thus, we fit loop closure data to a two-step kinetic model to extract these rates (data not shown). At 150 mM salt we measured a room-temperature on-rate of $4.0\pm0.7\times10^6$ $M^{-1}s^{-1}$. Combining our on-rate and off-rate measurements, we calculated a dissociation constant of $2.94\pm0.51\times10^{-13}$M, an equilibrium free energy change. $\Delta G^0$, of $-17.1\pm0.1$ kcal/mol, and an equilibrium enthalpy change, $\Delta H$, of $26.01\pm0.05$ kcal/mol (data not shown). In general, our measurements are consistent with values reported in the literature (data not shown). Specifically, we are within 15% of the reported off-rate of a biotin-labelled oligonucleotide[9], within 30% of on-rate measurements from SPR[11], and within 5% of both equilibrium $\Delta H$ measurements by ITC[12] and equilibrium $\Delta G$ measurements made by monitoring kinetics of radiolabeled biotin[13].

Without modifying the DNA construct, we were also able to measure kinetic and equilibrium properties for avidin and Neutravidin (data not shown). Although Neutravidin's affinity for biotin is 20 times weaker than avidin's, they surprisingly have similar off-rates (data not shown), underscoring the limitation of relying solely on affinity measurements to characterize an interaction.

To demonstrate the measurement of weaker interactions, we incorporated desthiobiotin, a biosynthetic precursor to biotin that binds streptavidin with far lower affinity[14]. By optimizing gel running conditions, we resolved the looped and unlooped constructs in as little as 6 minutes, measuring the off-rate of streptavidin-desthiobiotin as $35.3\pm7.5$ minutes at 4° C. and $8.6\pm1.2$ minutes at room temperature (data not shown). We note that while the system is ideal for quantification of long lived interactions, even those out of the range of biacore (data not shown), the time required to resolve the bands in a gel currently sets the lower limit of detectable dissociation life-times to minutes.

The modularity of the DNA construct facilitates the easy incorporation of different types of molecules. We exploited this feature to measure several biologically relevant interactions including enzymes with time constants of seconds to minutes, DNA, antibodies, small molecules, and even a covalent bond taking weeks to dissociate (data not shown). As with many techniques including SPR, assay preparation requires the derivatization of at least one molecule of interest. Here, we attach our molecule to a DNA oligonucleotide, which can be accomplished using a variety of techniques. In addition to SMCC-crosslinking[5], we previously described the use of click-chemistry to attach peptides to oligonucleotides, and the use of the enzyme sortase[15] to rapidly and efficiently attach proteins to our nanoswitches while preserving protein function[16].

The platform's versatility is facilitated by its universal readout—even as the molecules, temperatures, and buffer conditions for the interactions change, the "signature" gel readout does not. As an extreme example of this, we characterized the reduction of a disulfide bond at 25° C. in 10 µM TCEP yielding a time constant of $2.6\pm0.4$ weeks (data not shown). Since the signal per molecule is only dependent on the nanoswitch size, this two-atom system yields the same level of signal per interaction as a 150 kDa antibody binding to its antigen (data not shown).

Additionally, the programmability of these nanoswitches enables the design of multiple topological states that are individually distinguished on a gel, facilitating the analysis of complex multicomponent interactions (data not shown). We engineered nanoswitches with three integrated ligands, placed strategically to form two asymmetric loops when simultaneously bound by a bispecific receptor. The resulting nanoswitch adopts 5 resolvable states that can be identified with control experiments (data not shown). We measured bi-directional transitions for all 5 states, thus determining all rate constants (data not shown). This ability to monitor the fraction of molecules populating each state over time would be difficult or impossible to achieve with most other measurement techniques.

This new approach expands the biomedical researcher's toolbox, enabling low-cost, accessible, and parallel multi-component biomolecular interaction analysis using a basic laboratory technique, gel electrophoresis. We have demonstrated our platform's ability to characterize interactions with time constants ranging from seconds to months (~6 orders of magnitude), for a wide variety of molecular interactions, temperatures and buffer conditions (data not shown). The signals are robust and highly amplified, giving detection limits in the range of attomoles and allowing quantitative kinetic- and thermodynamic-analysis of proteins as shown here with femtomoles of material (~1 ng for a 50 kDa protein). In contrast to other techniques that provide one signal to analyze (e.g. SPR, radiolabeling, and ITC), we further differentiate our technique by showing independent measurement of 5 signals simultaneously in a unique multidimensional readout, allowing complete characterization of a complex 5-state system. The modularity and programmability of the nanoswitches affords control over the relative concentrations and stoichiometries of interacting components, independent of the nanoswitch concentration. This feature suggests that in addition to monitoring reactions, this system could be used as a template-directed synthesis technique to control complex reactions. Overall, this unique lab-on-a-molecule platform promises to be a powerful research tool, accessible to anyone able to perform gel electrophoresis.

EXAMPLE REFERENCES

1. Thorne, H. V. Virology. 29, 234-239 (1966).
2. Bishop, D. H. L., Claybrook J. R. & Spiegelman S. J. Mol. Bio. 26, 373-387 (1967).
3. Smithies, O. Biochem J. 61, 629-641 (1955).
4. Hellman, L. M. & Fried, M. G. Nat. Prot. 2, 8 (2007).
5. Halvorsen K., Schaak D. & Wong W. P. Nanotechnology. 22, pp. 1-8 (2011).
6. Saccà, B. & Niemeyer, C. M. Angew. Chem. Int. Ed. 51, 58-66 (2012).
7. Seeman, N. C. Annual Reviews Biochemistry. 79, 65-87 (2010).
8. Aaij, C. & Borst P. BIOCHIMICA ET BIOPHYSICA ACTA. 269, 192-200 (1972).
9. Levy, M. & Ellington, A. D. Chemistry & Biology. 15, 979-989 (2008).
10. Prabhu, N. V. & Sharp, K. A. Annual Reviews Physical Chemistry. 56, 521-48 (2005).
11. Qureshi, M. H., Yeung, J. C., Wu, S. C. & Wong. S. L. J Biol Chem. 276, 46422-46428 (2001).
12. Klumb, L. A., Chu, V. & Stayton P. S. Biochemistry. 21, 7657-63 (1998).
13. Chivers, C. E. et al. Nature Methods. 7, 391-393 (2010).
14. Florin, E. L., Moy V. T., and Gaub H. E. Science. 264, 415-417 (1994).
15. Chen I., Dorr, B. M., and Liu D. R. Proc. Natl. Acad. Sci. USA 108, 11399-11404 (2011).
16. Koussa M. A., Sotomayor M., Wong W. P. Methods. 67 134-141 (2014).
17. Strunz T, Oroszlan K, Schäfer R. & Güntherodt HJ. Proc. Natl. Acad. Sci. USA 96 11277-11282(1999).

EQUIVALENTS

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion. i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of." or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A. and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended. i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

---

What is claimed is:

1. A method comprising contacting (1) a nucleic acid complex conjugated to a first binding partner and a second binding partner with (2) a candidate ligand conjugated to a nucleic acid barcode, isolating a nucleic acid complex having the first binding partner bound to (a) the second binding partner and (b) the candidate ligand, and identifying the candidate ligand bound to the first binding partner by nucleic acid sequencing of the nucleic acid barcode, wherein the nucleic acid complex comprises a single-stranded scaffold nucleic acid hybridized to a plurality of single-stranded oligonucleotides, wherein a first single-stranded oligonucleotide in the plurality is linked to the first binding partner and a second single-stranded oligonucleotide in the plurality is linked to the second binding partner, and wherein the first binding partner and the second binding partner do not bind to each other unless the candidate ligand is bound to the first binding partner.

2. The method of claim 1, wherein identifying the candidate ligand comprises nucleic acid amplification of the nucleic acid barcode.

3. The method of claim 1, wherein the candidate ligand is in solution.

4. The method of claim 1, wherein the candidate ligand is linked to a third single-stranded oligonucleotide in the nucleic acid complex.

5. The method of claim 1, further comprising covalently attaching the candidate ligand to the first binding partner after the contacting step.

6. A method comprising contacting (1) a plurality of nucleic acid complexes each conjugated to a first binding partner and a second binding partner with (2) a plurality of candidate ligands each conjugated to a distinct/unique nucleic acid barcode, physically separating (1) nucleic acid complexes having the first binding partner bound to the second binding partner and to the candidate ligand from (2) other nucleic acid complexes, and identifying the candidate ligand bound to the first binding partner by nucleic acid sequencing of the nucleic acid barcode, wherein each nucleic acid complex comprises a single-stranded scaffold nucleic acid hybridized to a plurality of single-stranded oligonucleotides, wherein a first single-stranded oligonucleotide in the plurality is linked to the first binding partner and a second single-stranded oligonucleotide in the plurality is linked to the second binding partner, wherein the first binding partner and the second binding partner do not bind to each other unless the candidate ligand is bound to the first binding partner.

7. The method of claim 6, wherein the nucleic acid complexes are identical to each other.

8. The method of claim 6, wherein the plurality of candidate ligands is a library of candidate ligands.

9. A method comprising contacting a target with a candidate ligand conjugated to a nucleic acid barcode, wherein the target and optionally the candidate ligand are bound to a nucleic acid complex that is further bound to an active-target-specific binding partner and an inactive-target-specific binding partner, isolating a target bound to a candidate ligand and an active-target-specific binding partner, and identifying the candidate ligand bound to the target by nucleic acid sequencing of the nucleic acid barcode, wherein the nucleic acid complex comprises a single-stranded scaffold nucleic acid hybridized to a plurality of single-stranded oligonucleotides, wherein a first single-stranded oligonucleotide is linked to the target and a second single-stranded oligonucleotide is linked to the active-target-specific binding partner, wherein the target does not bind to the active-target-specific binding partner in the absence of the candidate ligand.

10. The method of claim 9, wherein the candidate ligand is linked to a third single-stranded oligonucleotide in the nucleic acid complex.

11. The method of claim 9, wherein the candidate ligand is in solution.

12. The method of claim 9, wherein the candidate ligand is covalently linked to the target to which it is bound prior to isolating.

13. The method of claim 9, wherein the target is covalently linked to the bound active-target-specific binding partner prior to isolating.

14. A method comprising contacting (1) a nucleic acid complex conjugated to a first binding partner and a second binding partner with (2) a candidate ligand conjugated to a nucleic acid barcode, wherein the first binding partner has affinity for the second binding partner in the absence of the candidate ligand, isolating a nucleic acid complex having the first binding partner bound to the candidate ligand and not bound to the second binding partner, and identifying the candidate ligand bound to the first binding partner by nucleic acid sequencing of the nucleic acid barcode, wherein the nucleic acid complex comprises a single-stranded scaffold nucleic acid hybridized to a plurality of single-stranded oligonucleotides, wherein a first single-stranded oligonucleotide in the plurality is linked to the first binding partner and a second single-stranded oligonucleotide in the plurality is linked to the second binding partner,

wherein the second binding partner and the candidate ligand are different from each other.

15. The method of claim 14, wherein wherein identifying the candidate ligand comprises nucleic acid amplification of the nucleic acid barcode.

16. The method of claim 14, wherein the candidate ligand is in solution.

17. The method of claim 14, wherein the candidate ligand is linked to a third single-stranded oligonucleotide in the nucleic acid complex.

18. The method of claim 14, further comprising covalently attaching the candidate ligand to the first binding partner after the contacting step.

19. The method of claim 14, wherein the first binding partner is directly bound to the second binding partner prior to contact with the candidate ligand, and upon direct binding to the candidate ligand the first binding partner dissociates from the second binding partner.

\* \* \* \* \*

36